(12) United States Patent
Johnson

(10) Patent No.: US 11,980,635 B2
(45) Date of Patent: May 14, 2024

(54) METHODS OF ORAL ADMINISTRATION OF PROTOCATECHUIC ACID FOR TREATING OR REDUCING THE SEVERITY OF A JOINT INJURY OR DISEASE

(71) Applicant: Lanny Leo Johnson, Henderson, NV (US)

(72) Inventor: Lanny Leo Johnson, Henderson, NV (US)

( * ) Notice: Subject to any disclaimer, the term of this patent is extended or adjusted under 35 U.S.C. 154(b) by 0 days.

(21) Appl. No.: 17/933,580

(22) Filed: Sep. 20, 2022

(65) Prior Publication Data

US 2023/0109279 A1    Apr. 6, 2023

Related U.S. Application Data

(63) Continuation-in-part of application No. 15/839,491, filed on Dec. 12, 2017, now abandoned, which is a continuation of application No. 14/533,820, filed on Nov. 5, 2014, now abandoned.

(51) Int. Cl.
*A61K 31/7048*   (2006.01)
*A61K 31/192*    (2006.01)

(52) U.S. Cl.
CPC ........ *A61K 31/7048* (2013.01); *A61K 31/192* (2013.01)

(58) Field of Classification Search
None
See application file for complete search history.

(56) References Cited

U.S. PATENT DOCUMENTS

| | | | |
|---|---|---|---|
| 4,997,850 | A | 3/1991 | Kimura et al. |
| 5,621,009 | A | 4/1997 | Watanabe et al. |
| 9,486,468 | B2 | 11/2016 | Johnson |
| 2006/0147564 | A1 | 7/2006 | Kim |
| 2010/0196331 | A1 | 8/2010 | Johnson |

FOREIGN PATENT DOCUMENTS

CN    101306003 A    3/2011

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
All references U.S. Appl. No. 15/839,491 per 37 CFR 1.98(d)(1).
All references U.S. Appl. No. 14/533,820 per 37 CFR 1.98(d)(1).
Ahmed S., "Biological Evidence for the Benefit of Green Tea and EGCG in Arthritis " Curr. Rheumatol. Rev. (2009) vol. 5, pp. 259-265.
Alvarez-Soria M. et al "Long term NSAID treatment inhibits COX-2 synthesis in the knee synovial membrane of patients with osteoarthritis: differential proinflammatory cytokine profile between celecoxib and acedofenac", Ann. Rheum. Dis. (2006) vol. 65, pp. 998-1005.
Anderson D. et al "Post-Traumatic Osteoarthritis: Improved Understanding and Opportunities for Early Intervention", J. Orthopaed. Res., vol. 29, No. 6, pp. 802-809. (Year: 2011).
Attur M. et al "Prostaglandin E2 Exerts Catabolic Effects in Osteoarthritis Cartilage: Evidence for Signaling via the EP4 Receptor", J. Immunol., vol. 181, pp. 5082-5088. (Year: 2008).
Bajpayee AG, Grodzinsky AJ., Abstract "Cartilage-targeting drug delivery: can electrostatic interactions help?", Nat Rev Rheumatol. 2017;13:183-93.
Bao J. et al "Lubricin: a novel potential biotherapeutic approaches for the treatment of osteoarthritis", Mol. Biol. Rep. (2011) vol. 38, pp. 2879-2885.
Chiusaroli R. et al "Experimental pharmacology of glucosamine sulfate" Int. J. Rheumatol., vol. 2011, pp. 1-8. (Year: 2011).
D'Lima DD, Hashimoto S, Chen PC, et al., "Prevention of chondrocyte apoptosis", J Bone Joint Surg Am. 2001;83:S25-26.
Deighton C. et al "Management of rheumatoid arthritis: summary of NICE guidance", BMJ (2009) vol. 338, pp. 710-712.
Ding Q. et al "Anti-arthritic effects of crocin in interleukin-IP-treated articular chondrocytes and cartilage in a rabbit osteoarthritic model", Inflamm. Res. (2013) vol. 62, pp. 17-25.
Dougados M. et al "Evaluation of the Structure-Modifying Effects of Diacerein in Hip Osteoarthritis", Arthritis & Rheumatism, vol. 44, No. 11, pp. 2539-2547. (Year:2001).
Goldberg V. et al "Hyaluronans in the treatment of osteoarthritis of the knee: evidence for disease-modifying activity" , Osteoarth. Cartilage, vol. 13, pp. 216-224. (Year: 2005).
Grimberg A., "Mechanisms by which IGF-I may promote cancer", Cancer Biol Ther. 2003;2:6, 630-635.
Hayami T. et al "Inhibition of cathepsin K reduces cartilage degeneration in the anterior cruciate liganlent transection rabbit and nurine lnodels of osteoarthritis", Bone, vol. 50, pp. 1250-1259 (Year: 2012).
Hickey DG, Frenkel SR, Di PC., Abstract "Clinical applications of growth factors for articular cartilage repair", Am J Orthop. 2003;32(2):70-76.
Hoemann et al., "International Cartilage Repair Society (ICRS) Recommended Guidelines for Histological Endpoints for Cartilage Repair Studies in Animal Models and Clinical Trials", Cartilage 2(2) 153-172.
Jotanovic Z. et al "Role of interleukin-1 inhibitors in osteoarthritis" Drugs Aging (2012) vol. 29, No. 5, pp. 343-358.
Krane et al., "Mechanisms of Matrix Degradation in Rheumatoid Arthritis", Department of Medicine Harvard Medical School and The Medical Services ( Arthritis Unit) Massachusetts General Hospital Boston, Massachusetts 02114.

(Continued)

*Primary Examiner* — Dale R Miller
(74) *Attorney, Agent, or Firm* — Stonebridge IP, PLLC

(57) ABSTRACT

The present disclosure describes a prophylactic method for the prevention of injury or disease of a synovial joint in a mammal that includes orally administering a composition including protocatechuic acid and a pharmaceutically acceptable carrier. The composition includes at least 0.035 mmol protocatechuic acid per kilogram bodyweight of the mammal. The orally administered composition increases insulin-like growth factor-1 (IGF-1) in the synovial fluid of a synovial joint of the mammal. The administration of the compound also increases insulin-like growth factor-1 (IGF-1) in the bloodstream of the mammal.

15 Claims, 48 Drawing Sheets

(56) References Cited

OTHER PUBLICATIONS

Lende A. et al "Anti-inflammatory and analgesic activity of protocatechuic acid in rats and mice" Inflammopharmacol. (2011) vol. 19, pp. 255-263.

Li Y, Wang Y, Chubinskaya S, Schoeberl B, Florine E, Kopesky P, et al., "Effects of insulin-like growth Factor-1 and dexamethasone on cytokine-challenged cartilage: relevance to post traumatic osteoarthritis", osteoarthritis. 2015;23(2):266-274.

Lin C Y. et al "Antiglycative Effects of Protocatechuic Acid in the Kidneys of Diabetic Mice", J. Agric. Food Chem., vol. 59, No. 9, pp. 5117-5124, (Year: 2011).

M. P. J. van den Borne et al., "International Cartilage Repair Society (ICRS) and Oswestry macroscopic cartilage evaluation scores validated for use in Autologous Chondrocyte Implantation (ACI) and microfracture", Osteoarthritis and Cartilage (2007) 15, 1397-1402.

Malemud C. "Anticytokine therapy for osteoarthritis" Drugs Aging (2010) vol. 27, No. 2, pp. 95-115.

Martin JA, Ellerbroek SM, Buckwalter JA., Abstract "Age-related decline in chondrocyte response to insulin-like growth factor-I: the role of growth factor binding proteins", J Orthop Res. 1997;15:491-8.

Min S. et al "Anti-inflammatory effects of black rice, cyanidin-3-O-β-D glycoside, and its metabolites, cyanidin and protocatechuic acid", Int. Immunopharmacol. (2010) vol. 10, pp. 959-966.

Morales TI, Hascall VC, "Factors involved in the regulation of proteoglycan metabolism in articular cartilage", Arthritis Rheum. 1989;32(10):1197-1201.

Noack W. et al "Glucosamine sulfate in osteoarthritis of the knee", Osteoarth. Cartilage, vol. 2, pp. 51-59. (Year: 1994).

Oh CD, Chun JS, "Signaling mechanisms leading to the regulation of differentiation and apoptosis of articular chondrocytes by insulin-like growth factor-1", J Biol Chem. 2003;278(38):36563-36571.

Pierre Mainil-Varlet, "Histological Assessment of Cartilage Repair: A Report By the Histology Endpoint Committee Ofthe International Cartilage Repair Society (ICRS)", The Journal of Bone and Joint Surgery, vol. 85-A supplement 2, Feb. 2003.

Rudolphi K. et al "Pralnacasan, an inhibitor of interleukin-1β converting enzyme, reduces joint damage in two murine models of osteoarthritis" OsteoArthritis and Cartilage (2003) vol. 11,pp. 738-746.

Rutkute K. et al "Regulation of insulin-like growth factor binding protein-1 expression during aging", Biochem. Bio phys. Res. Comm. (2007) vol. 361, pp. 263-269.

Sandy J D, Lowther D A, Brown H L G, Abstract "Antigen-induced arthritis: studies on the inhibition of proteoglycan synthesis observed in articular cartilage during short-term joint inflammation", Arthritis Rheum 1980; 23: 433-47.

Schalkwijk J. et al., Abstract "Chondrocyte nonresponsiveness to insulin-like growth factor 1 in experimental arthritis", Arthritis and rheumatism, [s. l.], v. 32, n. 7, p. 894-900, 1989.

Shakibaei M, Seifarth C, John J, et al, "Igf-I extends the chondrogenic potential of human articular chondrocytes in vitro: molecular association between Sox9 and Erk1/2", Biochem Pharmacol. 2006;2(11):1382-1395.

Snekhalatha U. et al "Evaluation of complete Freund's adjuvant-induced arthritis in a Wistar rat model", Z. Rheumatol. (2013) vol. 72, pp. 375-382.

T. L. McCarthy, M. Centrella, "Local IGF-I expression and bone formation", Growth Hormone & IGF Research 2001, 11, 213-219.

Van Den Berg et al., "Antigen-induced arthritis and zymosan-induced arthritis in mice: Studies on in vivo cartilage proteoglycan synthesis and chondrocyte death", BrJ Exp Pathol 1981; 62: 308-16.

Vedadghavami et al., "Cationic peptide carriers enable long-term delivery of insulin-like growth factor-1 to suppress osteoarthritis-induced matrix degradation", Arthritis Research & Therapy (2022) 24:172.

Wen et al., Insulin-like growth factor-1 in articular cartilage repair for osteoarthritis treatment, Arthritis Res Ther (2021) 23:277.

Wenham C. et al "Methotrexate for pain relief in knee osteoarthritis: an open-label study", Rheumatology (2013) vol. 52, pp. 888-892.

Wieland H. et al "Osteoarthritis: an untreatable disease?" Nat. Rev. Drug Disc., vol. 4, pp. 331-344. (Year: 2005).

Jörg Lützner, "Surgical options for patients with osteoarthritis of the knee", Nature Reviews Rheumatology, vol. Jun. 5, 2009, 311.

MedlinePlus, "Joint Disorders", National Library of Medicine, updated Dec. 13, 2021, https://medlineplus.gov/jointdisorders.html.

Wikipedia, "Arthropathy", the free encyclopedia, last edited on Jun. 10, 2022.

Wikipedia, "Preventive healthcare", the free encyclopedia, last edited on Sep. 14, 2022.

Wikipedia, "Protocatechuic acid", the free encyclopedia, last edited on Aug. 21, 2022.

Wikipedia, "Synovial joint", the free encyclopedia, last edited on May 19, 2022.

* cited by examiner

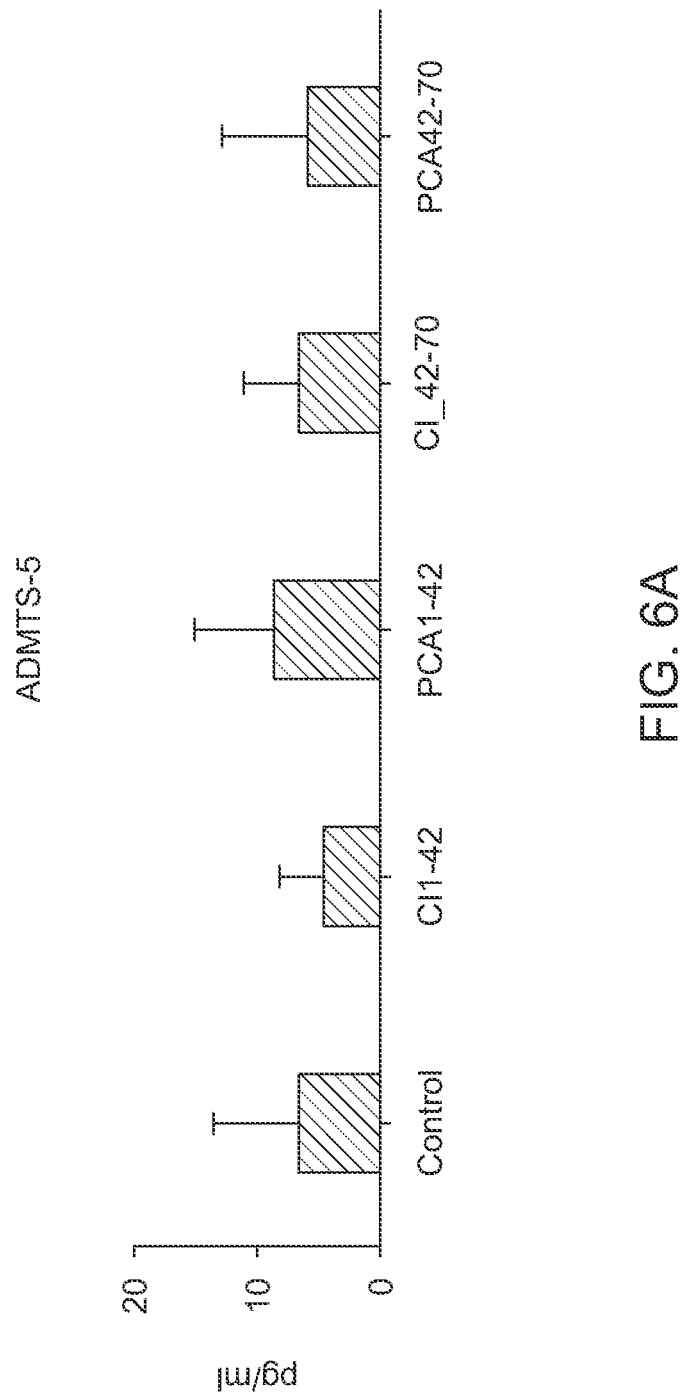

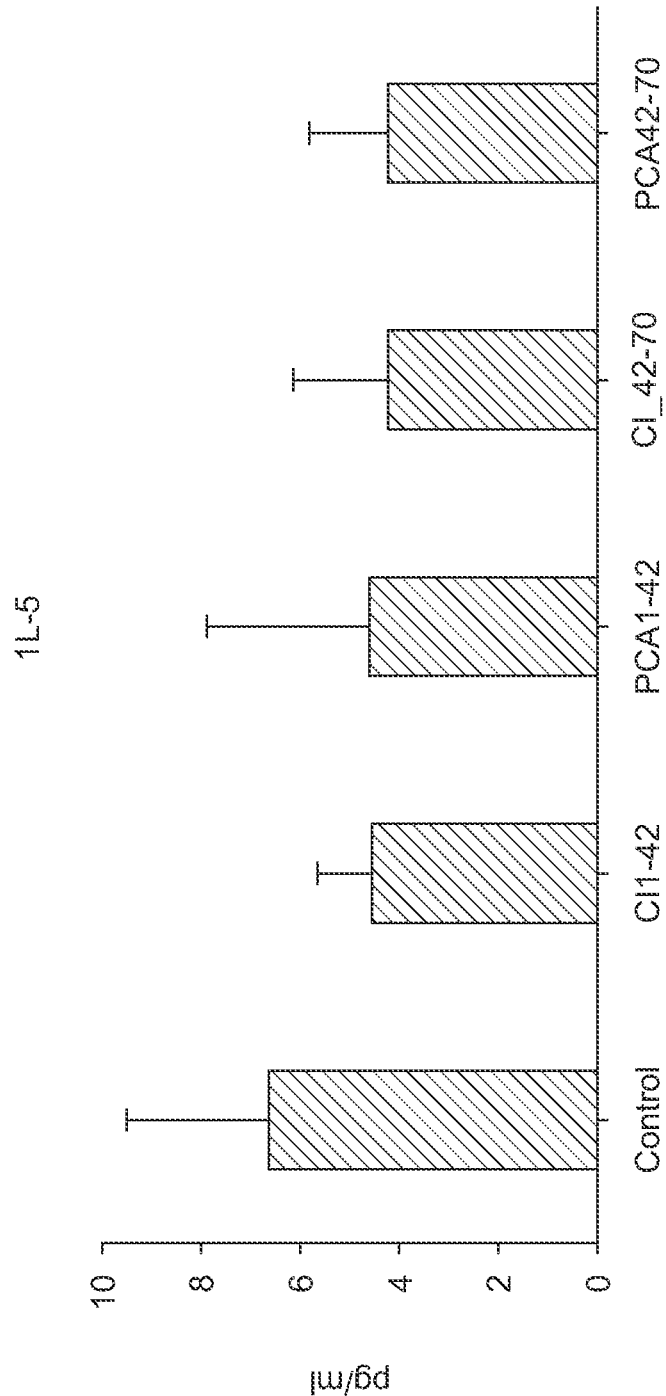

Figure 19: Lubricin expression was increased in the cartilage of all four groups Figure 21: ICRS histological visual scale. Surface scores improved for all groups Figure 22: ICRS histological visual scale. Matrix scores improved for all groups Figure 23: ICRS histological visual scale. Cell distribution improved for all groups Figure 24: ICRS histological visual scale. Cell viability remained the same for all groups Figure 25: ICRS histological visual scale. Subchondral bone score improved for all groups Figure 26: ICRS histological visual scale. Mineralization scores improved for all groups.

Figure 27: VEGF: Synovium

Figure 28: Il-10 Synovial Fluid

Figure 29: Il-4 Synovial Fluid

Phenolic acid (Vanillic acid) excretion in rabbits following oral gavage of control, cyanidin-3-glucoside (C-3-G)(10 mg/kg BW or Protocatechuic acid (3,4-dihydroxybenzoic acid) expressed as micrograms per mg creatinine in the urine sample Phenolic acid (Hippuric acid) excretion in rabbits following oral gavage of control, cyanidin-3-glucoside (C-3-G)(10 mg/kg BW or Protocatechuic acid (3,4-dihydroxybenzoic acid) expressed as micrograms per mg creatinine in the urine sample

METHODS OF ORAL ADMINISTRATION OF PROTOCATECHUIC ACID FOR TREATING OR REDUCING THE SEVERITY OF A JOINT INJURY OR DISEASE

CROSS-REFERENCE TO RELATED APPLICATIONS

This application is a continuation in part of U.S. Ser. No. 15/839,491, filed Dec. 12, 2017, which application is a continuation of U.S. Ser. No. 14/533,820, filed Nov. 5, 2014, with the disclosure of both prior applications incorporated herein by reference in their entireties.

BACKGROUND OF THE INVENTION

The homeostatic balance of the growth hormone IGF-1 in the synovial fluid is critical to the nutrition and integrity of the articular cartilage as it maintains equilibrium between synthesis and degradation of matrix proteoglycans. Therefore, there needs to be a prophylactic means of providing or even enhancing the nutrition and protection for cartilage matrix proteoglycan formation. The critical time for benefit of IGF-1 is known to be before injury or disease; prophylaxis. Evidence supports the prophylactic treatment of articular cartilage before an injury and or disease.

Insulin-like growth factor-1 (IGF-1) is the leading anabolic growth factor in cartilage and is important for structural maintenance via stimulation of cartilage matrix molecules. IGF-1 plays a primary role in articular cartilage, where it balances the synthesis of type II collagen and proteoglycans for chondrocyte regulation. IGF-1 protects chondrocytes from apoptosis.

Intra articular direct route of exogenous application of a drug is most common in the literature, but not generally effective in a single dose. Because of its localized nature, intra-articular (IA) administration results in most of the administered drug being rapidly removed through the lymphatics and synovium vasculature preventing them from reaching their cell and matrix target sites in cartilage.

Based upon the literature which is solely by exogenous application in vitro to cells or matrix or by exogenous intra-articular direct topical application, there is little expectation that IGF-1 treatment would support articular cartilage nutrition and or integrity. Delivery strategies that include a single intraarticular dose of IGF-1 even with various carriers like virus, have failed to be effective in targeting the articular cartilage and or produce a prolonged therapeutic effect. A single free intra articular injection of IGF-1 gives no protection to the articular cartilage. Unlike the literature's single direct application approach of IGF-1 to the synovium, this application's method is an indirect approach to increase the IGF-1 in the synovial joint. No IGF-1 is directly applied to the joint like those reporting in the literature anticipating drug development. In this application a food supplement, protocatechuic acid (PCA) is given by mouth. It is rapidly absorbed in the blood. PCA thereby reaches the synovial lining whereby a unique biological endogenous means PCA increases the genetic expression of the growth hormone IGF-1. This new method differs not only in route, but in dosage being multiple over a 6-weeks' time. The multiple treatment necessary is not likely to be implemented by the intra articular injection method.

SUMMARY OF THE INVENTION

The present invention provides oral formulations useful for prophylactic treatment of an injured or diseased joint. PCA, a nutraceutical can be taken as a prophylactic intervention. In embodiments, a prophylactic course can start before surgery of a joint occurs and continue on for a time period after a surgery. The formulations are as described herein below in more detail. In embodiments, the active ingredient comprises, consists essentially of, or consists of, protocatechuic acid (PCA).

The present invention provides methods of treating or decreasing inflammation of a joint in a mammalian subject, by orally administering to the subject a composition comprising a formulation or composition of the present invention. The composition has the effect of decreasing levels of MMP1, TFG-beta, and MMP13 in the synovial fluid of the joint and increasing the levels of TIMP-1, VEGF, IL-10 and Il-4 in the synovial fluid of the joint to cause a reduction of inflammation in the joint.

The inflammation in the joint is due to an injury or trauma to the joint or due to arthritis of the joint or due to inflammatory arthritis.

Protocatechuic acid (PCA) is a phytochemical, a powerful antioxidant, which is found in nature. There are no known human toxic effects of PCA. PCA is non-allergenic. It is also non-mutagenic. Importantly for a new prophylactic, protocatechuic acid (PCA) has been designated as Generally Recognized As Safe (GRAS) by the FDA as a food flavoring substance. PCA may be biochemically manufactured and/or extracted from plants in an amorphous or crystalline state. See e.g., Protocatechuic acid, Wikipedia, the free encyclopedia, last edited: 21 Aug. 2022, herein incorporated by reference.

Methods of formulating pharmaceutical compositions are generally known in the art and are applicable with the instant invention. For instance, the active ingredient may be mixed with a pharmaceutically acceptable carrier or salt. Formulation development and selection of pharmaceutically acceptable excipients, carriers, stabilizers, coloring, and flavoring agents and the like and can be found in a variety of pharmaceutical texts known to those skilled in the art, such as Remington's Pharmaceutical Sciences (Mack Publishing Co., Eaton, Pa.).

In certain embodiments, the route of administration is oral. Powdered active ingredient can be mixed with a suitable liquid for drinking or gavage or alternatively, the active ingredient can be in the form of a pill or capsule. The active ingredient may also be mixed with other solid eatable ingredients, such as for an example, in a nutrition/snack bar.

In certain embodiments, the oral administration comprises administering a daily dose for at least 6 weeks of a dose of 0.177 mmoles PCA per kg body weight (26.4 mg/kg). In certain embodiments, the oral administration comprises administering a daily dose for at least 10 weeks of a dose of 0.177 mmoles PCA per kg body weight (26.4 mg/kg). The oral administration comprises administering a daily dose for at least 4 weeks of a dose 0.177 mmoles PCA per kg body weight (26.4 mg/kg) starting after the injury. The treatment can begin any time.

In certain embodiments, the oral administration comprises 0.177 mmoles PCA per kg body weight (26.4 mg/kg) and continuing on for some time after a surgery. As one illustrative example, the daily dose may begin at least one week before surgery and continue for at least 4 weeks after surgery at the same dose. In certain embodiments the oral daily dosage ranges from 0.035 to 0.100 millimoles PCA of body weight. The oral daily dose can be given before surgery or before injury as a prophylactic treatment. The oral daily dose can be given during surgery and can be continued on after surgery or injury until the injury has healed. The oral daily dose can be given on a long-term basis as well.

In certain embodiments the oral daily dosage ranges from 0.100 to 0.200 mmol PCA per kg body weight. The oral daily dose can be given before surgery or before as a prophylactic treatment. The oral daily dose can be given during surgery and can be continued on after surgery. The oral daily dose can be given safely on a long-term basis for prophylactic reasons in anticipation of synovial joint deterioration due to injury and or disease.

The present invention also provides a novel prophylactic method that increases the genetic anabolic expression of IGF-1 in the synovial joint lining and synovial fluid and increases IGF-1 in the bloodstream. The result of this prophylactic treatment is improved nutrition and protection of the articular cartilage in mammals. A composition including administering protocatechuic acid by the oral route thereby biologically increases the genetic anabolic expression of IGF-1 in the synovial joint lining. The resultant increased amount of IGF-1 in the synovial fluid bathes the articular cartilage, thereby providing prophylactic protective nutrition to the articular cartilage.

Therefore, oral administration of PCA provides an unexpected result that is due, at least in part, to the method of delivery not being direct application to the cartilage by intraarticular injection (of IGF-1). The reason is the indirect increase of IGF-1 from the PCA oral route via blood to the synovial joint, action in harmony with the natural biological process of producing IGF-1 in the synovium by causing enhanced genetic expression of IGF-1. It does not require a prescription of multiple intraarticular injections over a period of time which is not practical when translated to clinical medicine.

Other features and aspects will be apparent from the following detailed description, the drawings, and the claims.

BRIEF DESCRIPTION OF DRAWINGS

FIG. 6A shows that ADAMTS-5 was decreased in the synovial fluid in both C3G groups and in the therapeutic PCA group.

FIG. 9C shows that IL-6 was decreased in the synovium in all groups.

Scores for all four groups improved.

Figure 27:
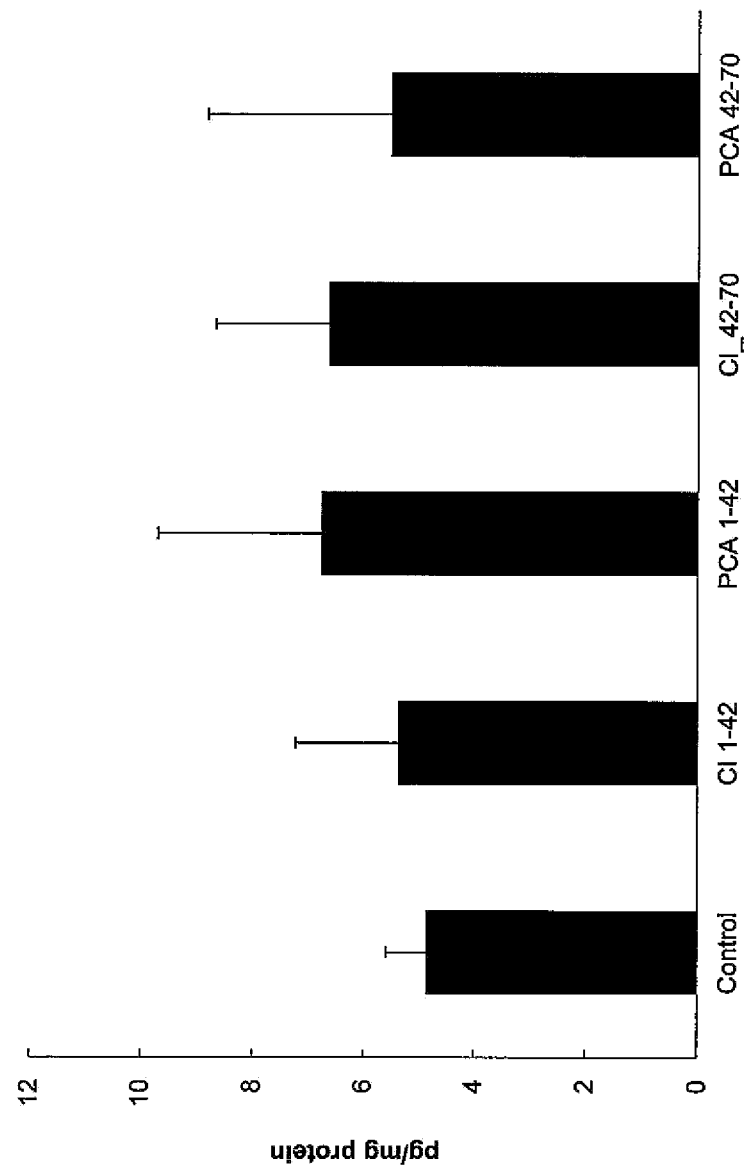

FIG. 27 shows that the levels of VEGF in the synovium were increased in all four groups.

Figure 28:
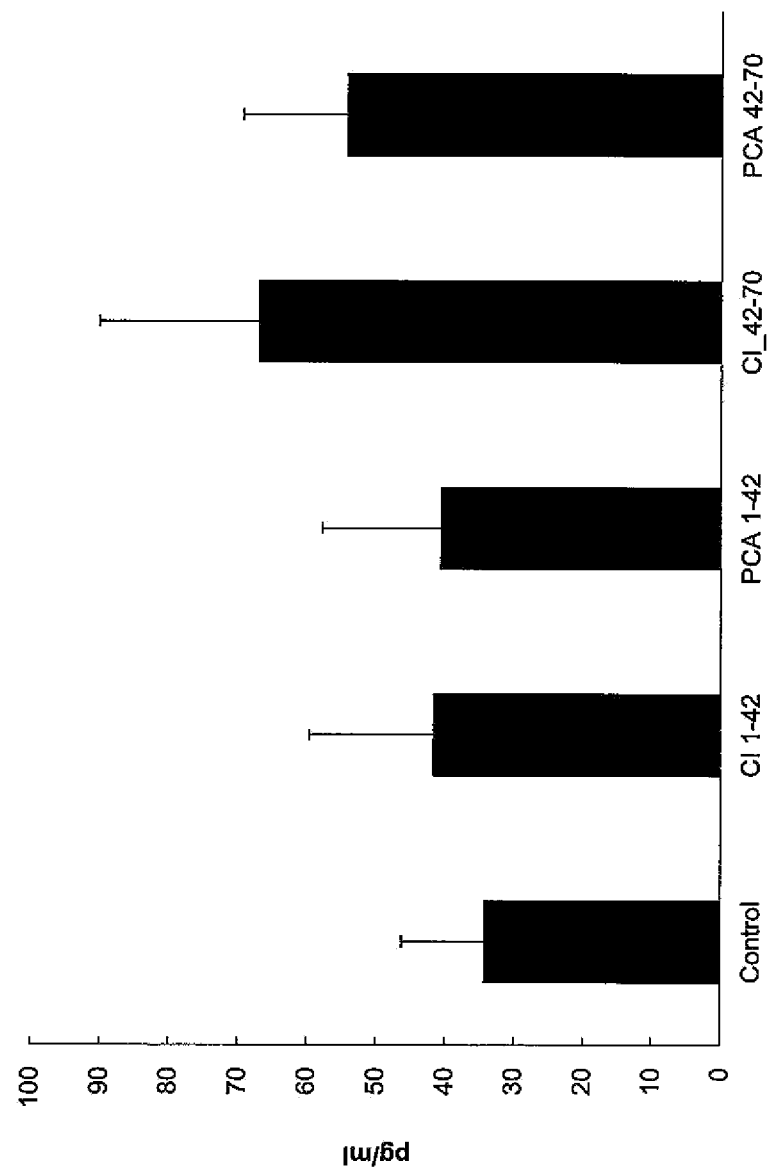

FIG. 28 shows that the levels of IL-10 in the synovial fluid were increased in all four groups.

Figure 29:
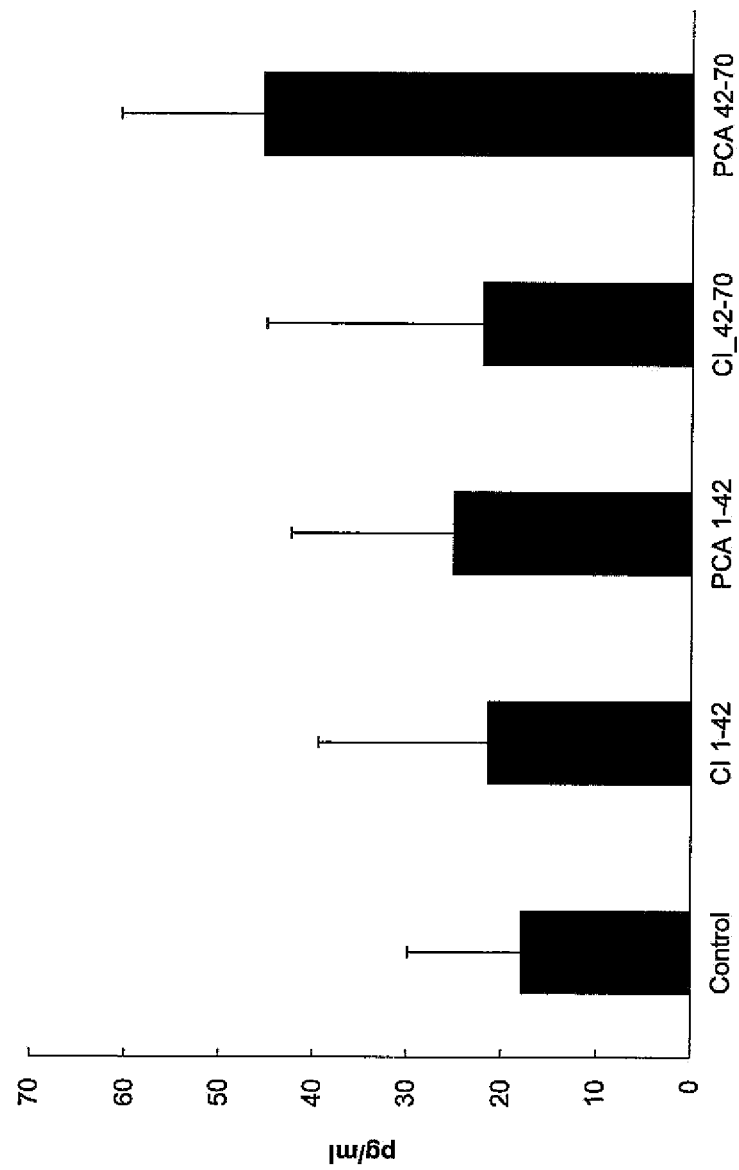

FIG. 29 shows that the levels of IL-4 in the synovial fluid was increased in all four groups.

Figure 30:
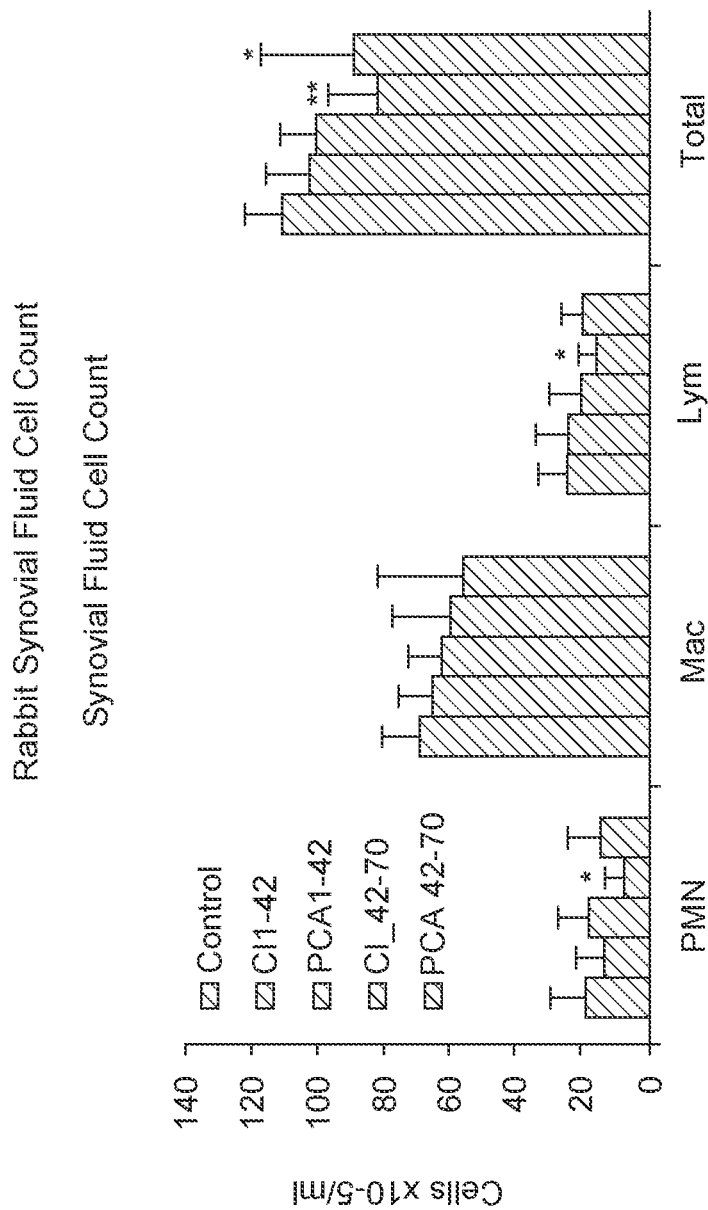

FIG. 30 shows that the total white blood cell count in the synovial fluid was decreased in all 4 study groups.

Figure 31A:
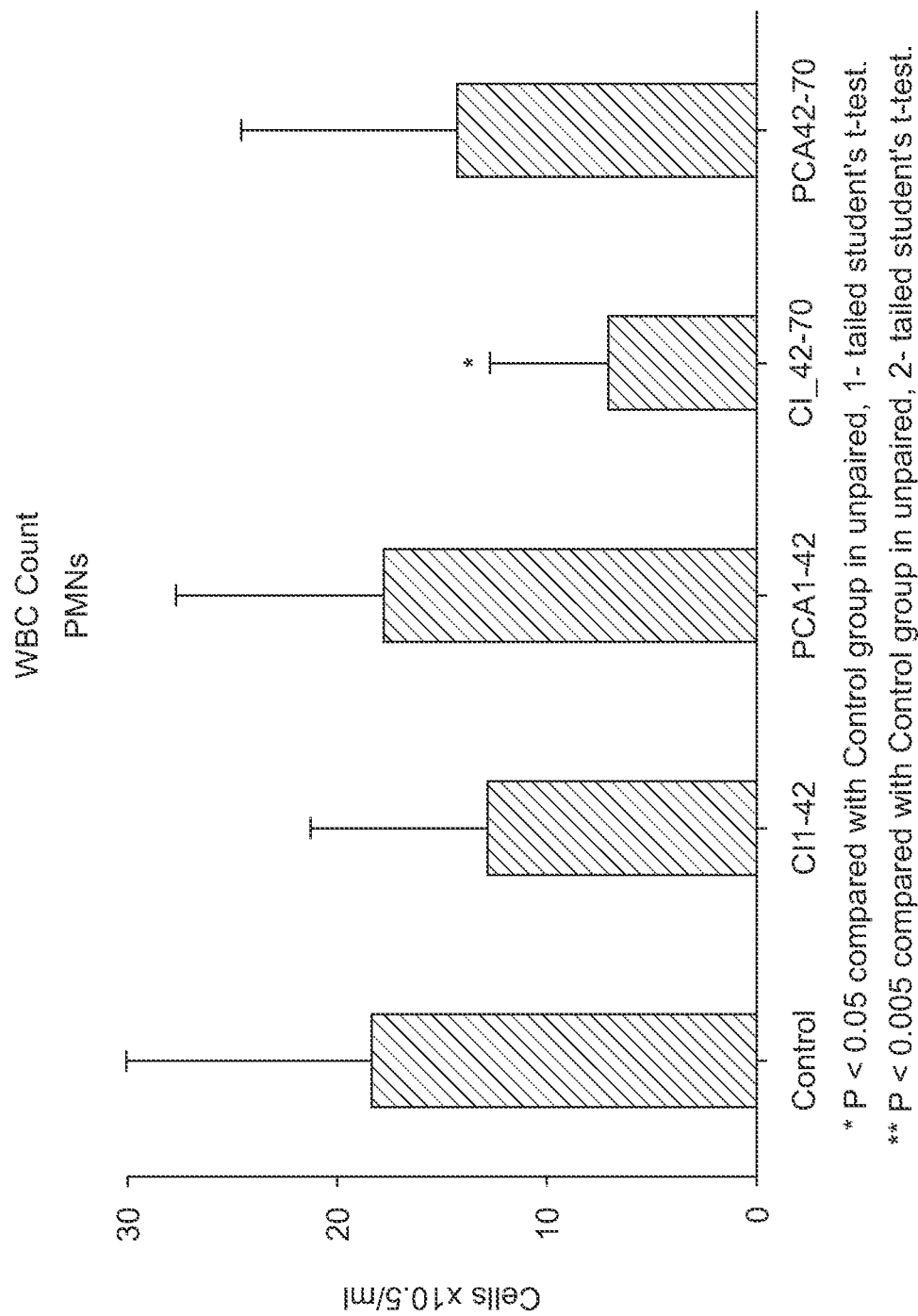

FIG. 31A shows that the number of PMN s was also reduced in the synovial fluid of all four groups, although most noticeable in the C3G groups.

Figure 31B:
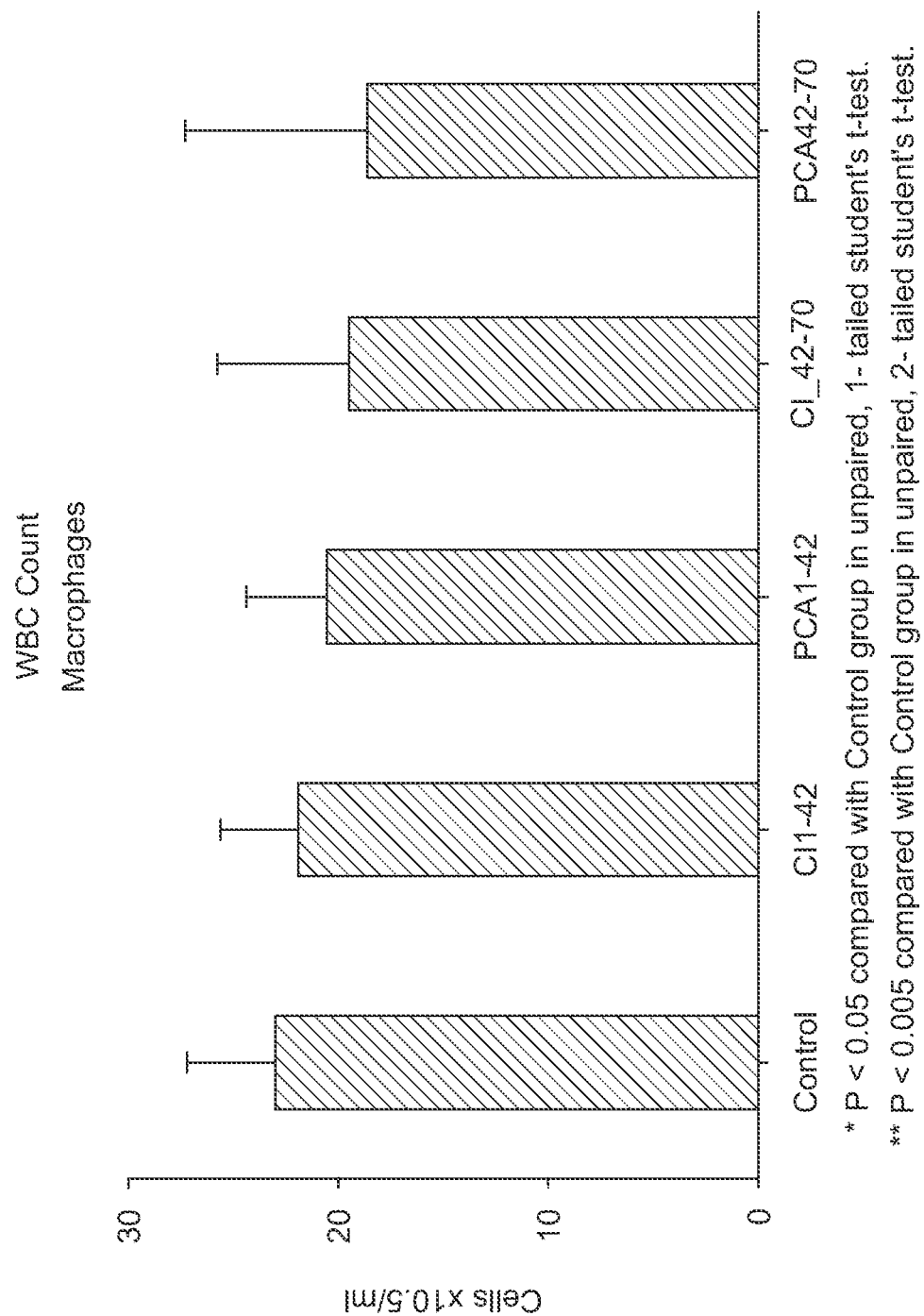

FIG. 31B shows that the number of macrophages was also decreased in all groups.

Figure 31C:
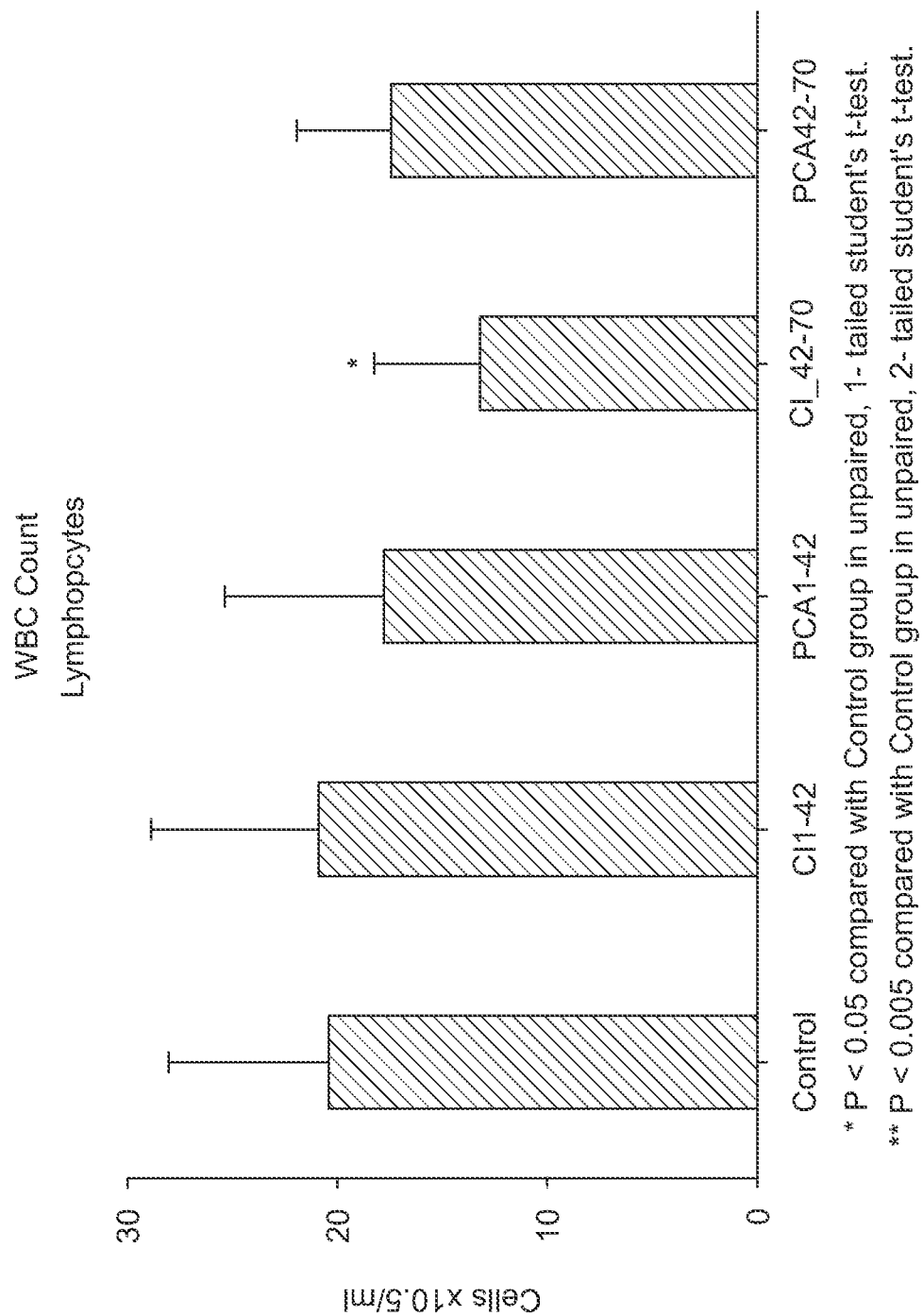

FIG. 31C shows that the number of lymphocytes in the synovial fluid was also decreased in 3 of the groups (both the G3G and PCT therapeutic group and the PCA prophylactic group).

Figure 31D:
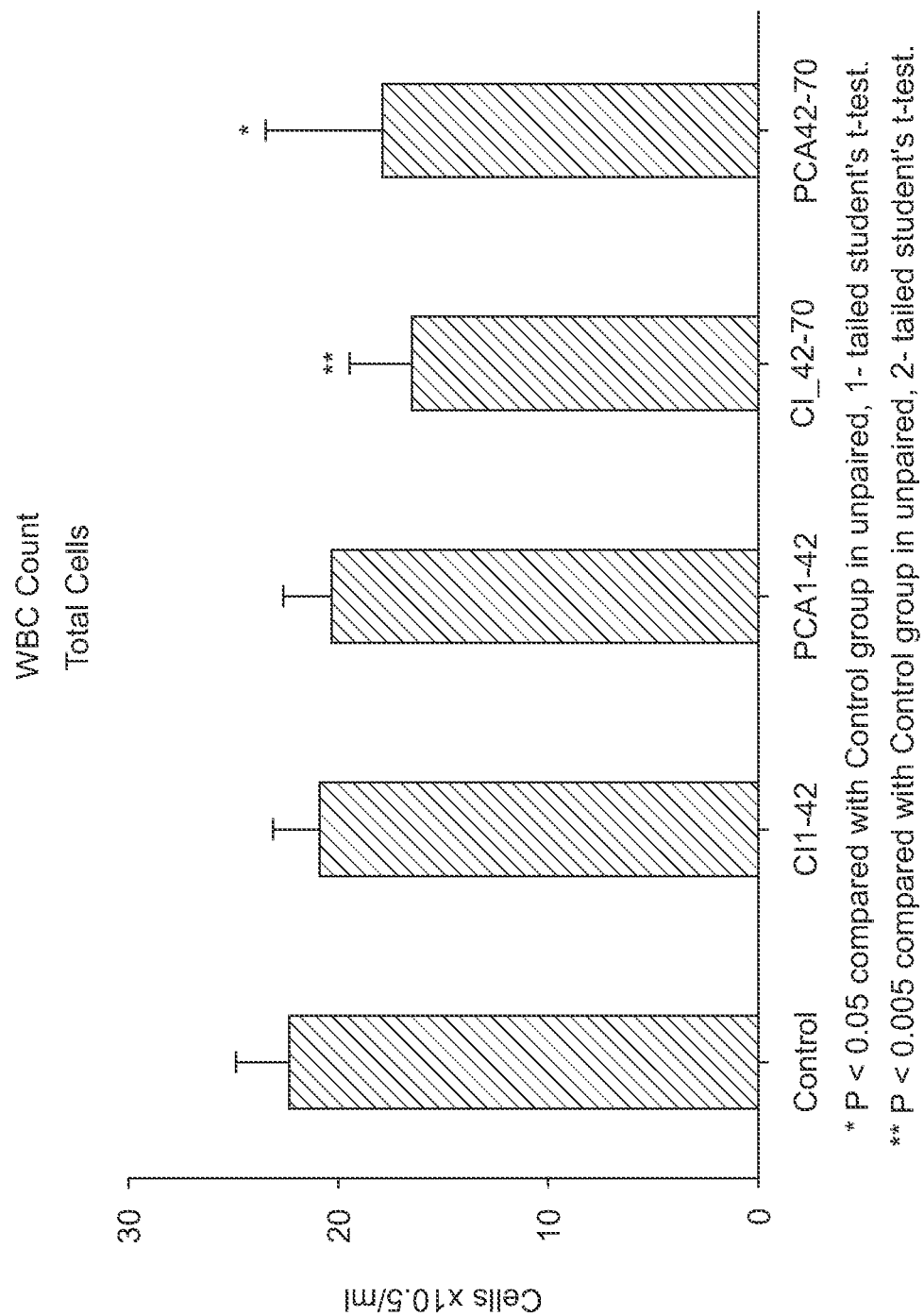

FIG. 31D shows that the total white blood cell count in the synovial fluid was decreased in all 4 study groups.

Figure 32A:
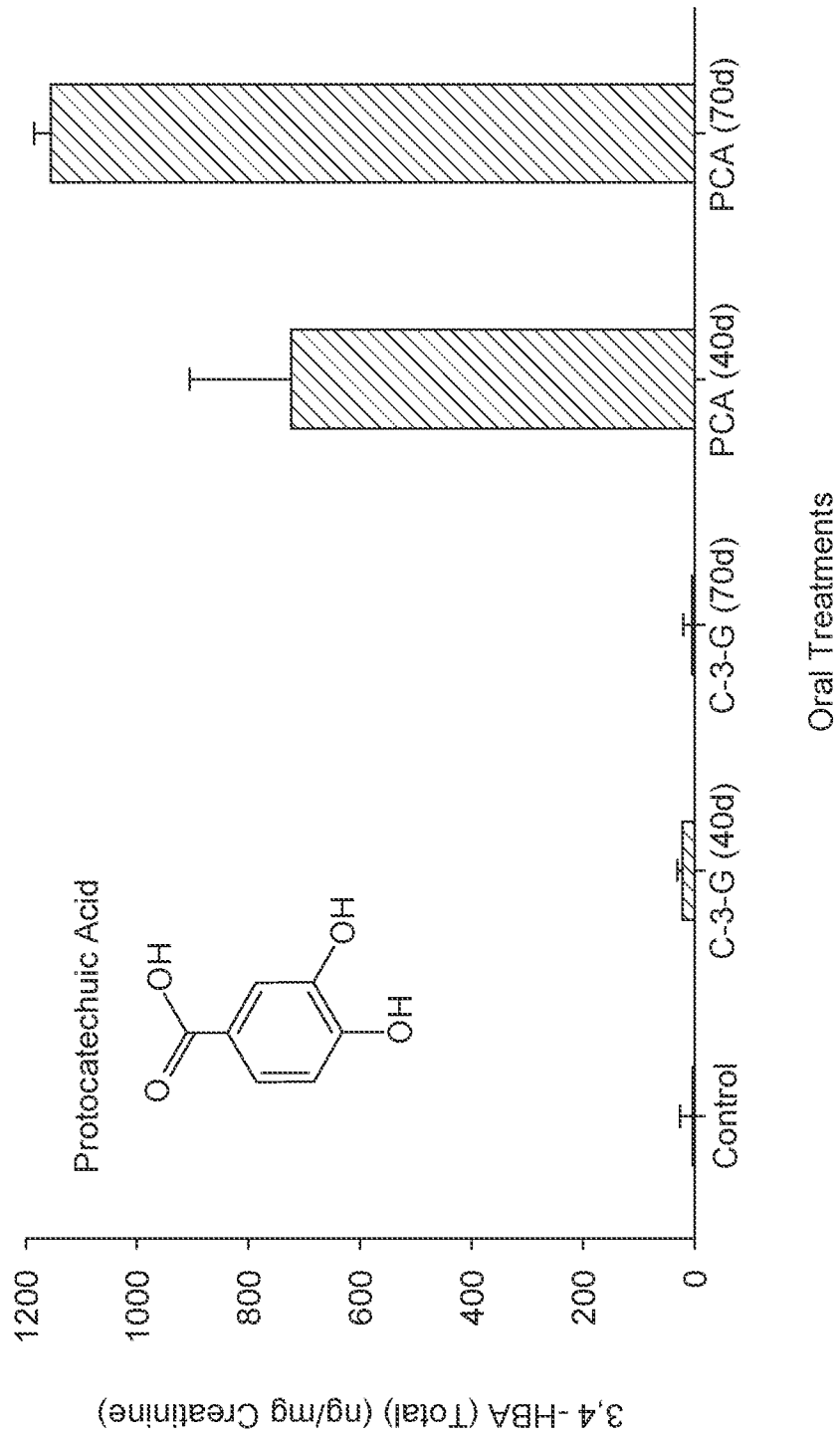
Figure 32B:
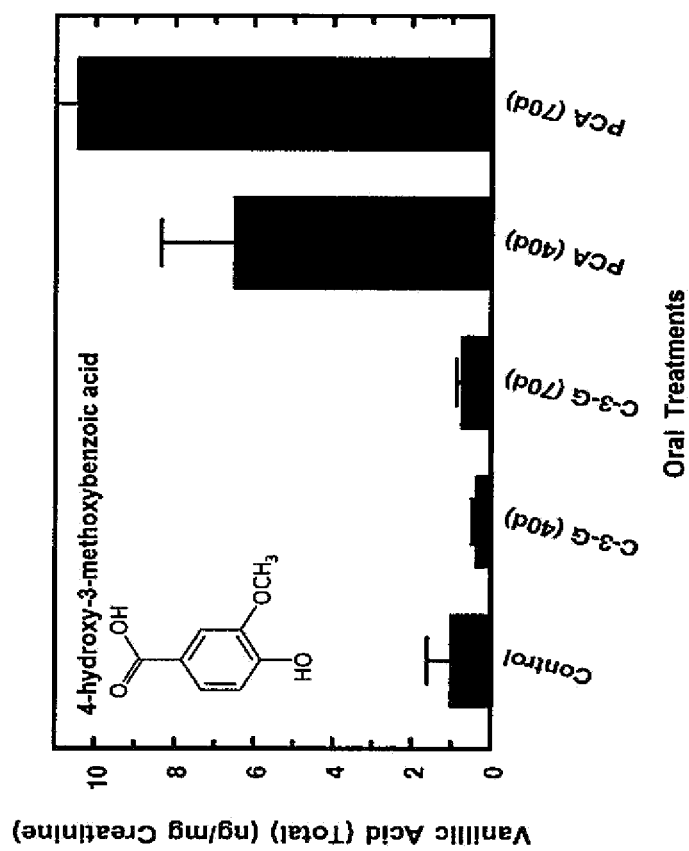
Figure 32C:
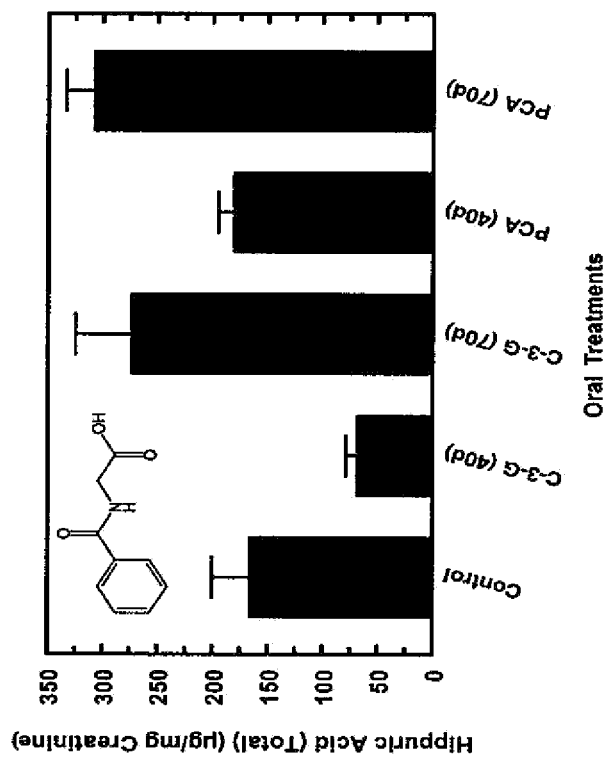

FIGS. 32A-C show Phenolic acid excretion in rabbits following oral gavage of control, cyanidin-3-glucoside (C-3-G)(30 mg/kg BW or Protocatechuic acid (3,4-dihydroxybenzoic acid)(26.4 mg/kg) expressed as micrograms per mg creatinine in the urine sample. FIG. 32A is for 3,4-HBA excretion. FIG. 32B is for Vanillic acid and 32C is for Hippuric acid.

FIGURE LEGENDS

Control: test subject did not receive any medication.

CI 1-42: prophylactic C3G group (test subjects received 30 mg C3G/kg Body weight ("BW") Chromadex Pro3CG™ by mouth 7 times per week for 42 days). PCA 1-42: prophylactic PCA group (test subjects received 26.4 mg (PCA)/kg BW by mouth 7 times per week for 42 days). C142-70: Therapeutic C3G group (test subjects received 30 mg (C3G)/kg of body weight Chromadex™ Pro3CG™ by mouth (starting on day 42 after surgery through day 70) 7 times per week for 4 weeks. PCA 42-70: Therapeutic PCA group (test subjects received 26.4 mg (PCA)/kg bodyweight by mouth (starting on day 42 after surgery through day 70) 7 times per week for 4 weeks.

DETAILED DESCRIPTION OF THE INVENTION

The structure and biology of articular cartilage of the synovial joint is unique among the tissues of the human mammalian body. It is defined as hyaline cartilage to differentiate it from fibrous cartilage as in a meniscus or elastic cartilage that is in the ear or costal cartilage which is more cellular with type I cartilage.

Articular cartilage of the hyaline nature is found in the synovial joint. Unlike most tissues it has no resident blood supply. It receives nutrition by diffusion from the synovial fluid and the supporting subchondral bone. It consists primarily of water suspended in a fibrous network identified as aggrecan and the uniquely a type II collagen. The main bulk of the structure is identified as the extra cellular matrix (ECM). Cells are singular, sparse, and widely distributed, and imbedded in the matrix.

The articular cartilage function is to support the joint integrity while promoting motion between two bones by the ECM mass. The motion is facilitated by lubricin, a unique surface lubricating protein. Lubricin's properties facilitate a smooth gliding motion between bones. The matrix mass by nature provides a cushioning effect to the loads transmitted across the synovial joint whether in motion or stationary. Articular cartilage is vulnerable to disruption due to injury, disease, or by genetic predisposition. One of the measures of disruption is the death of cartilage cells; apoptosis, which happens with injury.

The pathophysiology of disruption is the same, independent of the etiology. The first event is breakdown of the ECM by physical disruption or a fissure. Then fragmentation progresses to the surface whereby loose fragments are loosed into the synovial fluid. From there a vicious cycle results in progression of articular cartilage destruction.

Therefore, there is a need to support and optimize articular cartilage prior to injury, disease, or genetic predisposition. Absent the blood supply and with few widely spaced cells, the articular cartilage has limited repair or regenerative potential. It is totally dependent upon nutrition from the synovial fluid and the subchondral bone to maintain its integrity.

The literature only references treatments. The treatments using IGF-1 are by in vitro topical application and/or intra articular injection. The oral medications that are currently available are therapeutic and not prophylactic.

As with any disease condition, prophylactic measures are the best therapeutic measures. Current state of the art treatments provide no prophylactic means of protecting articular cartilage. There is no means of enhancing its nutrition or protecting its integrity.

It has long been recognized in the medical literature that IGF-1 plays a major role in articular cartilage metabolism. However, to date, no prophylactic or therapeutic clinical treatment has been implemented involving IGF-1. The research literature supporting the potential treatment of articular cartilage have been based upon the exogenous application of IGF-1. There has not been a protective use of IGF-1 by endogenous biological stimulation. In spite of all the various therapeutic attempts, the present-day definitive treatment for end stage loss of joint function remains artificial total joint replacement. There is thus a need in the art to nurture and protect articular cartilage thereby reducing the risk of surgery for end stage conditions.

The present invention provides a novel prophylactic method that relies on endogenous biological means, rather than an exogenous delivery of the growth hormone IGF-1 or any other reagent including PCA. The result of this treatment is improved nutrition and protection of the articular cartilage in mammals. Administering a phytochemical medication, protocatechuic acid, by the oral route thereby biologically increases the genetic anabolic expression of IGF-1 in the synovial joint lining. The resultant increased amount of IGF-1 in the synovial fluid bathes the articular cartilage, thereby providing prophylactic protective nutrition to the articular cartilage.

A pathological experimental model was chosen to establish PCA as a chondronutritive and chondroprotective prophylactic medication. This mode better demonstrated the chondronutritive and chondro-protective potential of PCA than an experimental model having a normal condition. The normal joint would not provide the same magnitude of potential change. The results confirmed the prophylactic benefit of prescription of a minimum of 30 mg/kilo gram body weight of protocatechuic acid by oral route. This resulted in an enhanced biological structure of the articular cartilage. Compared to the controls, the articular cartilage cells were unchanged in nature and spacing. There was increased EMC supporting aggrecan and type II collagen. There was increased lubricin on the surface. Importantly the subchondral bone remained normal in structure, without degenerative changes of sclerosis or osteophyte formation.

The term chondroprotective or chondroprotective agent as used herein refers to a process, substance or molecule that inhibits or reduces the degradation of cartilage or chondrocytes. The compositions also increased the all-important surface lubricant, lubricin, which promotes joint surface gliding, thereby reducing peak axial loads on the articular cartilage.

The term chondronutritive or chondronutritive agent as used herein refers to a process, substance or molecule that activates a cartilage cell to produce or enhances the production of glucopolysaccharides. The compositions of the invention are chondronutritive in that they increase the production of type II collagen, aggrecan and lubricin in the synovium.

The term chondroreparative or chondroreparative agent as used herein refers to a process, substance or molecule that causes cartilage to repair, such as with fibrocartilage. The compositions of the invention are chondroreparative because they increased the IGF-1 in the synovium and synovial fluid. IGF-1 arrests programmed cell death, apoptosis. In addition the compositions by way of optimizing the anabolic/catabolic nature of the synovial joint environment, they thereby maximize the chondronutrition and chondroprotection for cartilage healing by the increase in IGF-1 presence and, in the case of surgery (open or arthroscopic) or arthrocentesis the presence of bleeding providing blood, a common denominator for wound healing.

The term chondrorestorative agent as used herein refers to a process, substance or molecule that causes cartilage to be restored to its normal hyaline pattern or nature. A chondrorestorative agent restores or improves normal activities or functions to the cartilage. The compositions of the invention provide the optimal environment for chondrorestoration.

The terms prophylactic or prophylaxis refers to action taken for the purpose of disease or injury prevention. See e.g. preventative healthcare, Wikipedia, the free encyclopedia, last edited: 14 Sep. 2022, herein incorporated by reference.

The terms disease or injury of a joint refers to conditions and injuries that affect joints including conditions developed as a result of age and overuse as well as sudden injuries from accidents or a sports injury. See Athropathy, Wikipedia, the free encyclopedia, last edited: 10 Jun. 2022, herein incorporated by reference; and joint disorders, MedlinePlus, last updated Dec. 13, 2021, herein incorporated by reference.

The term synovial joint, also known as diarthrosis, joins bones or cartilage with a fibrous joint capsule that is continuous with the periosteum of the joined bones, constitutes the outer boundary of a synovial cavity, and surrounds the bones' articulating surfaces. The synovial cavity/joint is filled with synovial fluid. The joint capsule is made up of an outer layer of fibrous membrane, which keeps the bones together structurally, and an inner layer, the synovial lining or membrane, which seals in the synovial fluid. See synovial joint, Wikipedia, the free encyclopedia, last edited: 19 May 2022, herein incorporated by reference.

The term endogenously refers to being produced or synthesized from within an organism or system.

International Cartilage Repair Society (ICRS) criteria are described for example in Hoemann, et al. (cited on Applicant's IDS), herein incorporated by reference.

The Examples below demonstrate that protocatechuic acid given as an oral medication provided nutrition and protection of the articular cartilage of a mammalian synovial joint.

EXAMPLES

Example 1—Oral Ingestion Rabbit Study

The study was approved by the Institutional Animal Care and Use Committee (IACUC) of Thomas D. Morris, Inc. 28 New Zeeland White rabbits were selected for the study. Six such were randomly assigned to one of four groups; prophylactic cyanidin-3-glycoside (C3G)(referred to figures as CI 1-42), prophylactic protocatechuic acid (PCA)(referred to in figures as PCA 1-42), therapeutic C3G (referred to in figures as CI 42-70), and therapeutic PCA (referred to in figures as PCA 42-70). There were four controls, two each to the prophylactic and therapeutic groups. The controls did not receive any treatment.

The prophylactic groups were given PROC3G™ by Chromadex™ at a dose of 30 mg/kg of body weight of either C3G or PCA by mouth, 7 times per week for 42 days. The therapeutic groups' treatment was initiated on day 42 with a daily dose of PROC3G™ by Chromadex™ 7 times per week for 4 weeks. The dose of 30 mg of cyanidin-3-glucoside per kg of body weight calculates to be 0.177 millimoles per kg body weight. The dose of PCA was the same in terms of millimoles per kg body weight.

The experimental rabbits underwent surgery with an intent to create a severe degenerative arthritis by cutting the medial collateral ligament, the anterior cruciate ligament and removing the medial meniscus. A partial thickness laceration was made longitudinally on the lateral femoral condyle for future assessment of potential for repair. The surgery was performed by two licensed veterinarians. One surgeon was very experienced. The other surgeon was a recent graduate.

The magnitude of the arthritis was intentional in order to produce abundance of synovial reaction and synovial fluid for subsequent study. The experimental model was not designed for the likelihood of healing or cartilage repair due to the short time frame of the study.

At necropsy, the synovial fluid was harvested percutaneously and upon arthrotomy. The synovium was harvested from posterior compartment. The patella and adjacent synovium was procured as a separate specimen as was the medial and lateral condyle.

The synovial fluid and half of the synovium was frozen and sent to BioBoston Laboratory for chemical analysis. The other half of the synovium and bone was sent to McClinchery Histology in Stockbridge, Mich. for histological preparation and staining. Patellar slides were sent to BioBoston Contract Laboratories for histochemical staining and ICRS grading. Sample slides were examined for Lubricin at Myron Spector laboratory.

The cartilage status was subjected to a histological scale rating according to the International Cartilage Repair Society. Mainil-Varlet P, et al., The International Cartilage Repair Society (ICRS)—Histological Visual Scale. A preliminary Report of the Histological End Point Committee. I. Human Biopsies, Toronto Consensus. Europ Cells and Materials. Vol 4., Suppl. 1, 2002. (page 10).

Blood testing was performed prior to necropsy on C3G, PCA, glucose, MMP-3 and IGF-1 to assess any systemic effects.

Urine testing was performed prior to necropsy for C3G and PCA to assess the metabolic course. All reviews were performed by a blinded examiner.

Results

There were 20 rabbits available for bilateral tissue harvest. Four had partial tissue available (#9, 2, 8, and 15). There was no tissue on three; #1, 20, 28. One of the controls (#27) for the therapeutic groups required early euthanasia due to illness. One of the PCA (#10) therapeutic group was lost due to illness. One of the C3G therapeutic group (#28) died in recovery and another died during the course of the study. Three others specimens were compromised by dislocated knee in one case and dislocated patella in two. The surgery in the compromised animals was performed by the recent graduate licensed veterinarian.

There were 40 specimens sent from 20 rabbits for bilateral chemical analysis. There were three unilateral specimens. There were no specimens sent for histology on four animals; 10 #16, 20, 22, 28. Partial specimens were sent on #10 and 15.

There was no evidence of healing of the lateral femoral condylar surgically induced partial thickness laceration within the short duration of the study.

Various assays were performed to determine levels of certain biomolecules associated with inflammation (e.g. proinflammatory cytokines), anabolic or catabolic processes (e.g. IGF-1, EGF, TIMP, MMP-3, MMP-1, Adamts-5). These tests results are provided below.

MMP-3

MMP3 is known as matrix metallopeptidase 3, or stromelysin 1 or progelatinase. Proteins of the matrix metalloproteinase (MMP) family are involved in the breakdown of 20 extracellular matrix in normal physiological processes, such as embryonic development, reproduction, and tissue remodeling, as well as in disease processes, such as arthritis and metastasis. Most MMP's are secreted as inactive proproteins which are activated when cleaved by extracellular proteinases.

Synovial Fluid—Detected by ELISA

Figure 2A:
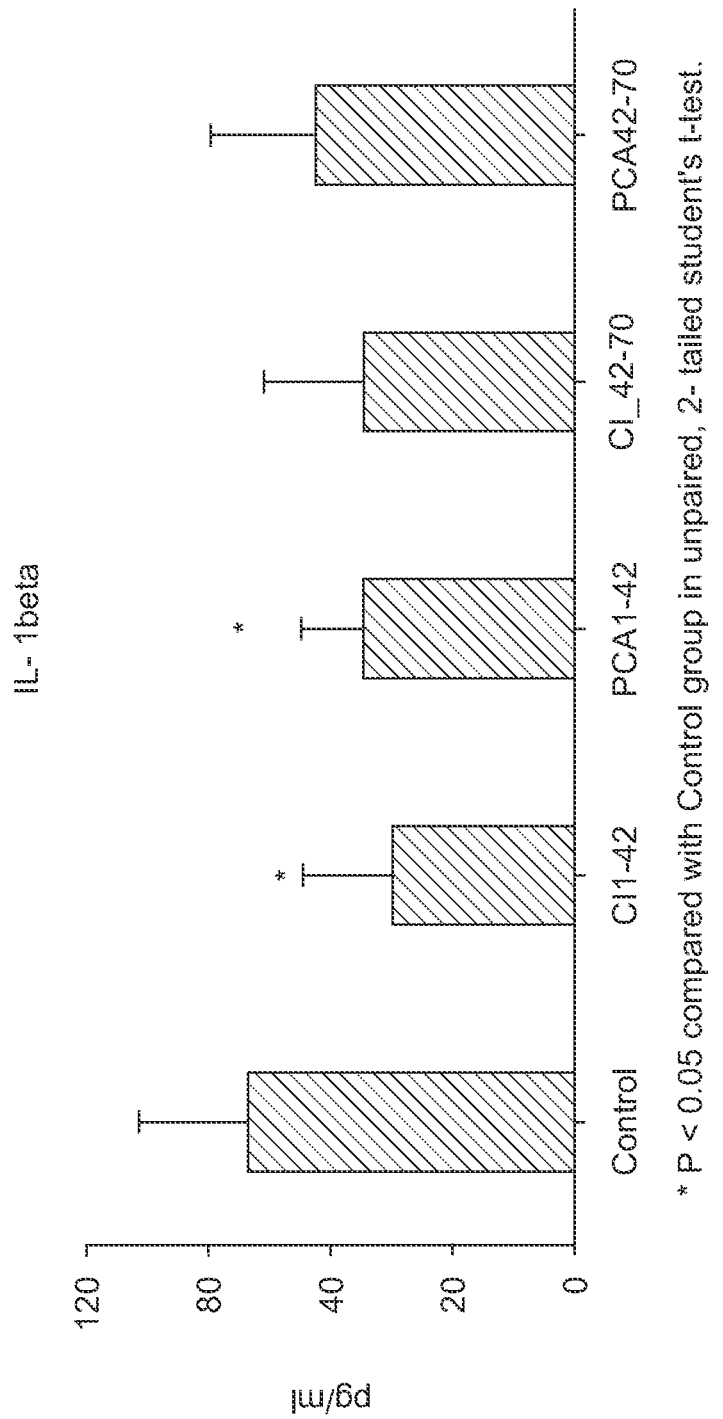
FIG. 2A shows that levels of IL-1 beta were decreased in the synovial fluid in all groups.
Figure 2B:
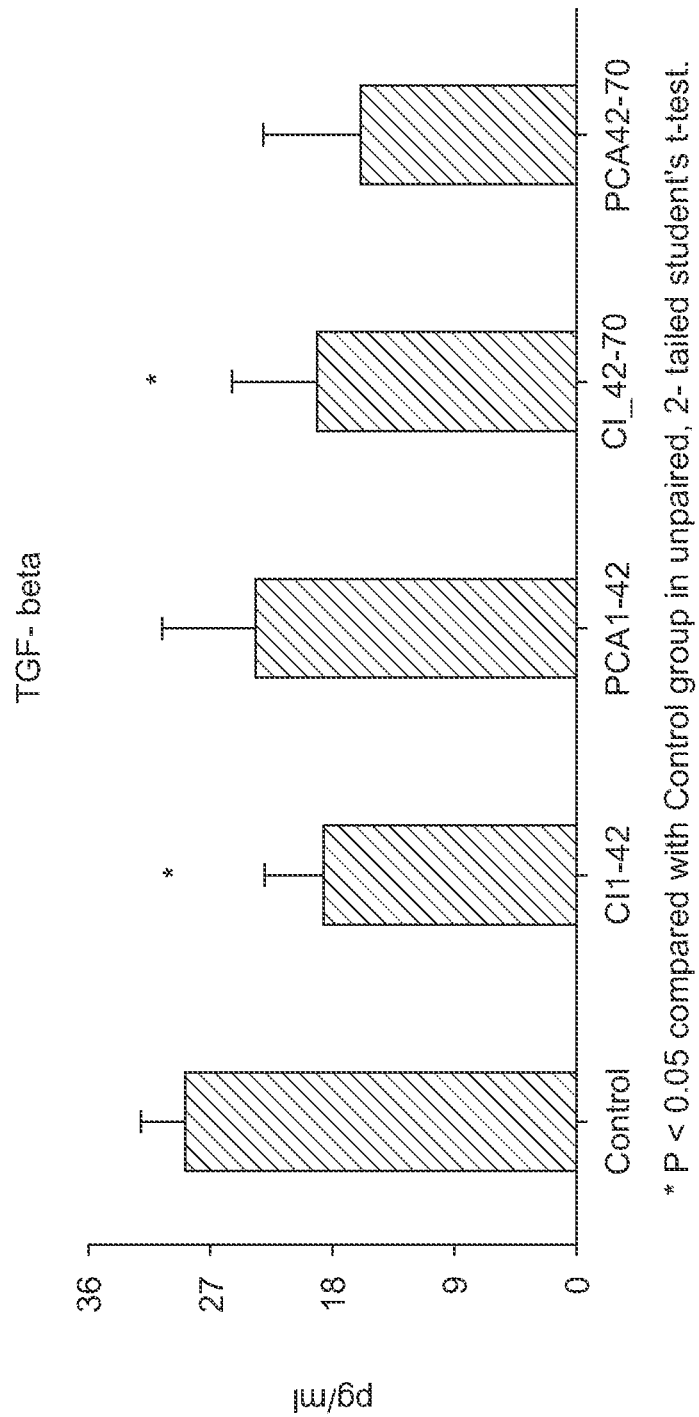
FIG. 2B shows that TGF-beta was decreased in the synovial fluid in all groups.
Figure 2C:
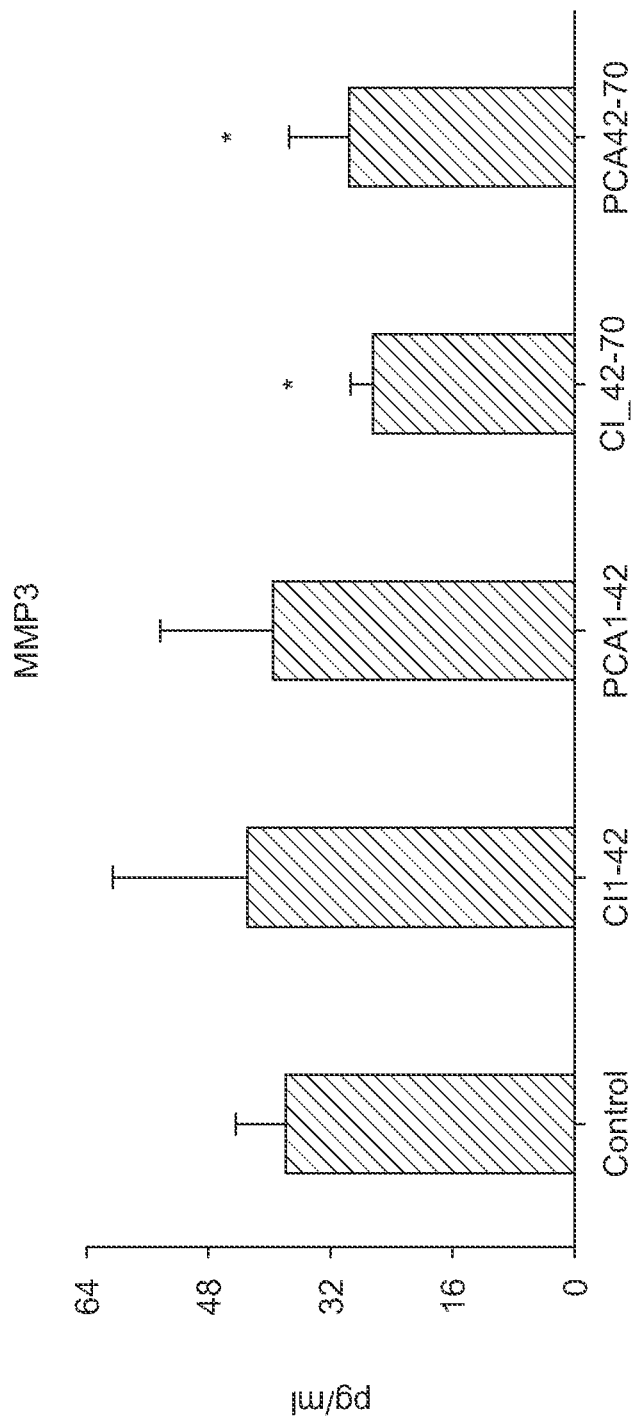
FIG. 2C shows that MMP3 was decreased in the synovial fluid for therapeutic groups for C3G and PCA.

MMP3 was decreased in the therapeutic groups for C3G and PCA. See FIG. 2C.

Synovial Tissue (Synovium)—Detected by ELISA

Figure 9A:
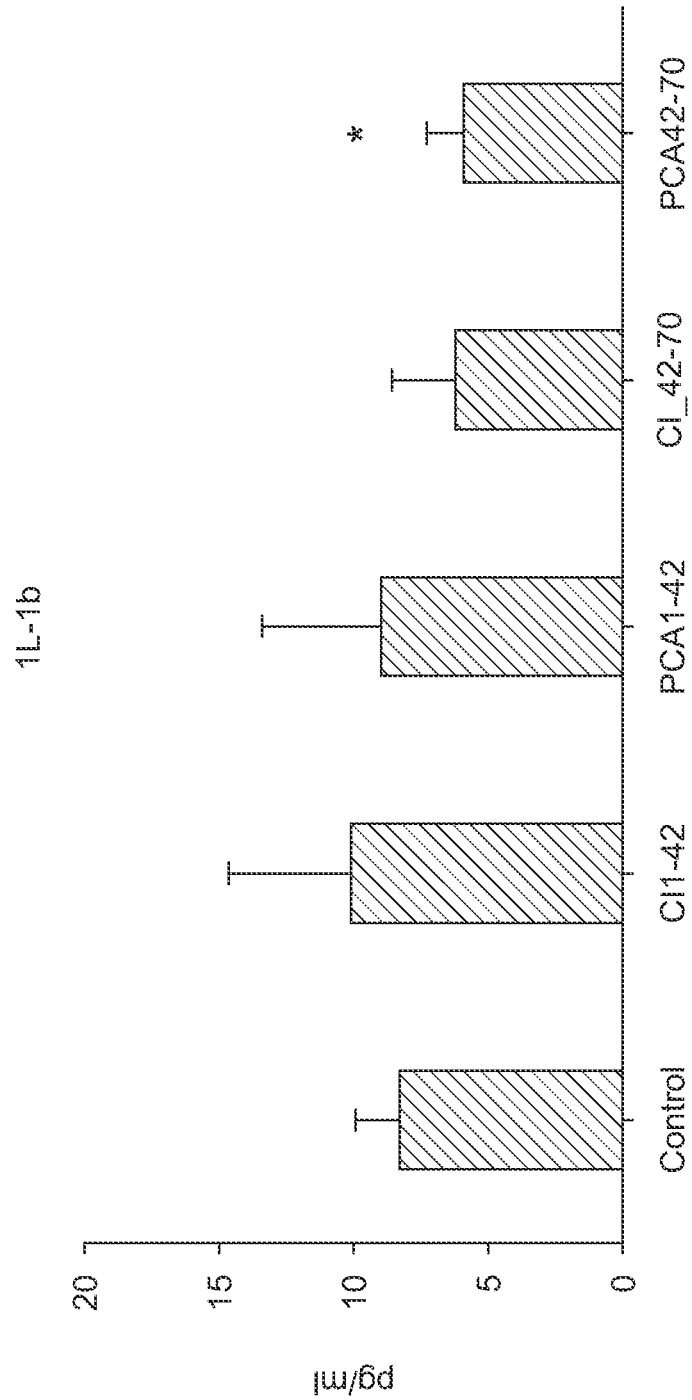
FIG. 9A shows that levels of IL-1 beta were decreased in the synovium of the C3G and PCA therapeutic groups but were increased in the two prophylactic groups.
Figure 9B:
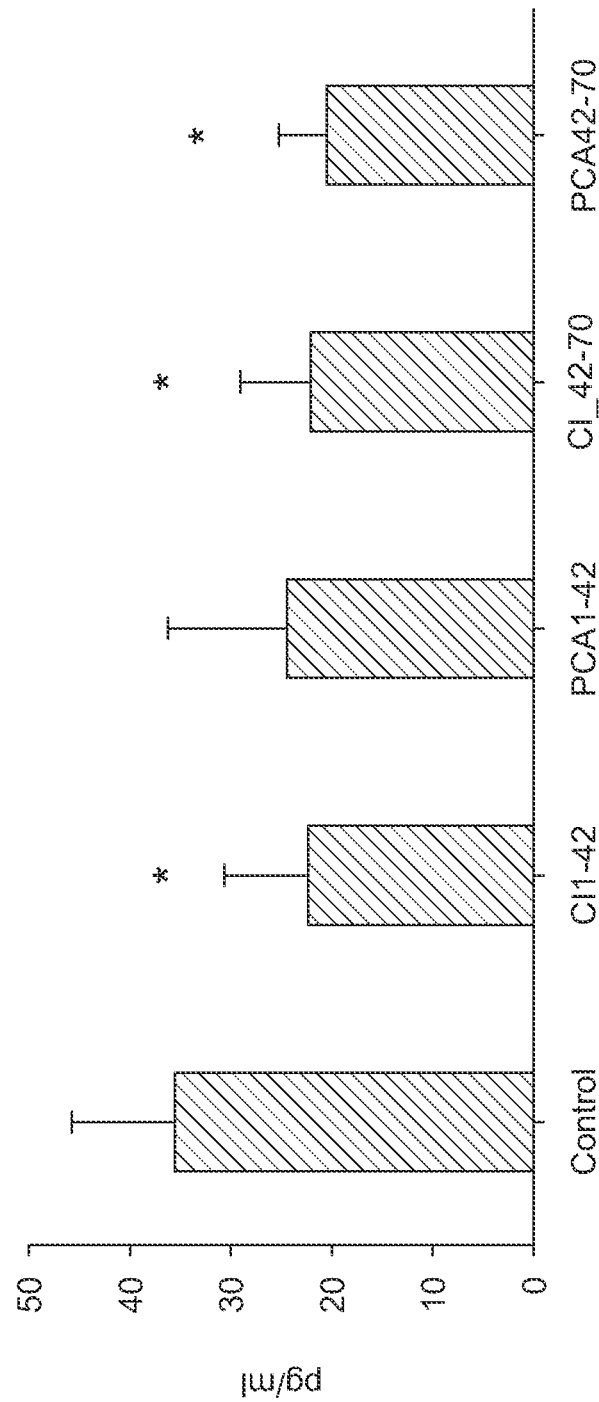
FIG. 9B shows that MMP-3 levels were reduced the synovium in all four groups.

MMP-3 levels were reduced in all four groups. See FIG. 9B.

Synovial Tissue (Synovium)—Gene Expression Level Detected by Real-Time PCR

Figure 13A:
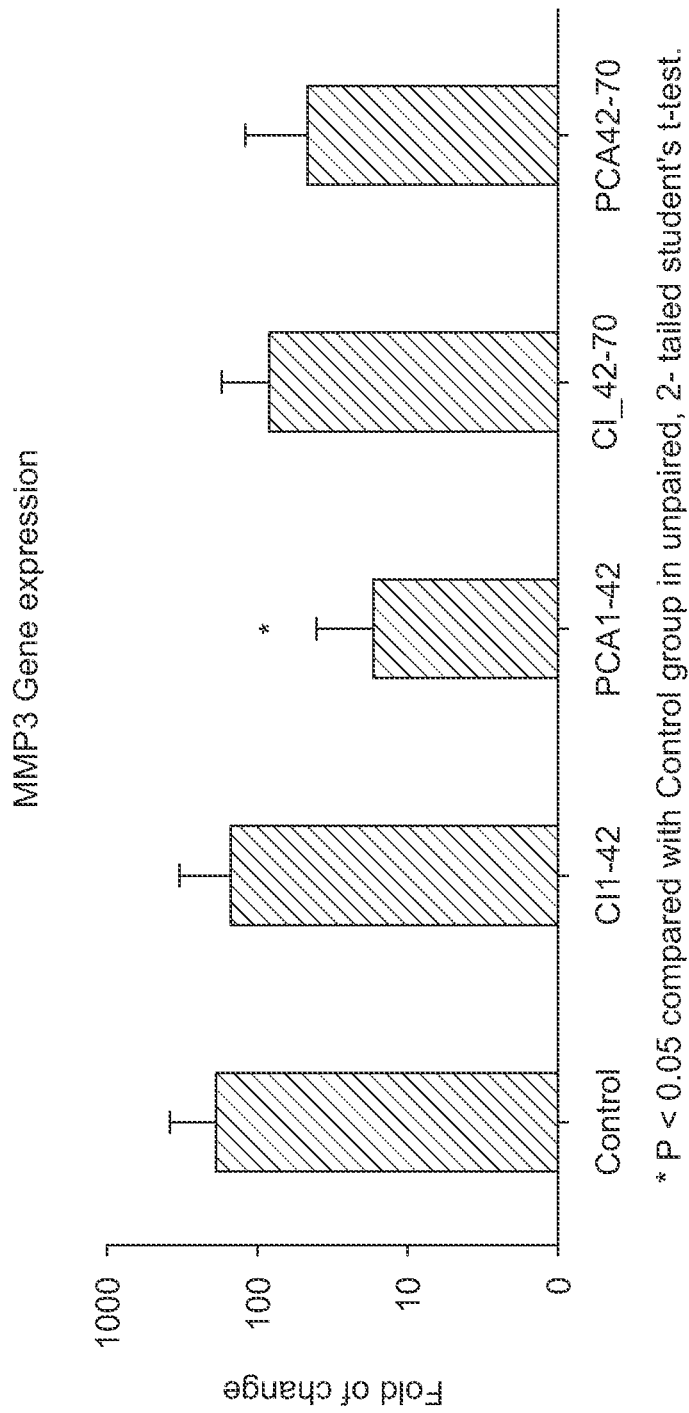
FIG. 13A shows that MMP-3 gene expression was decreased in the synovium as detected by real time PCT in all groups.

MMP-3 gene expression was decreased in all groups. See FIG. 13A.

Histochemical Scoring Analysis

Figure 3:
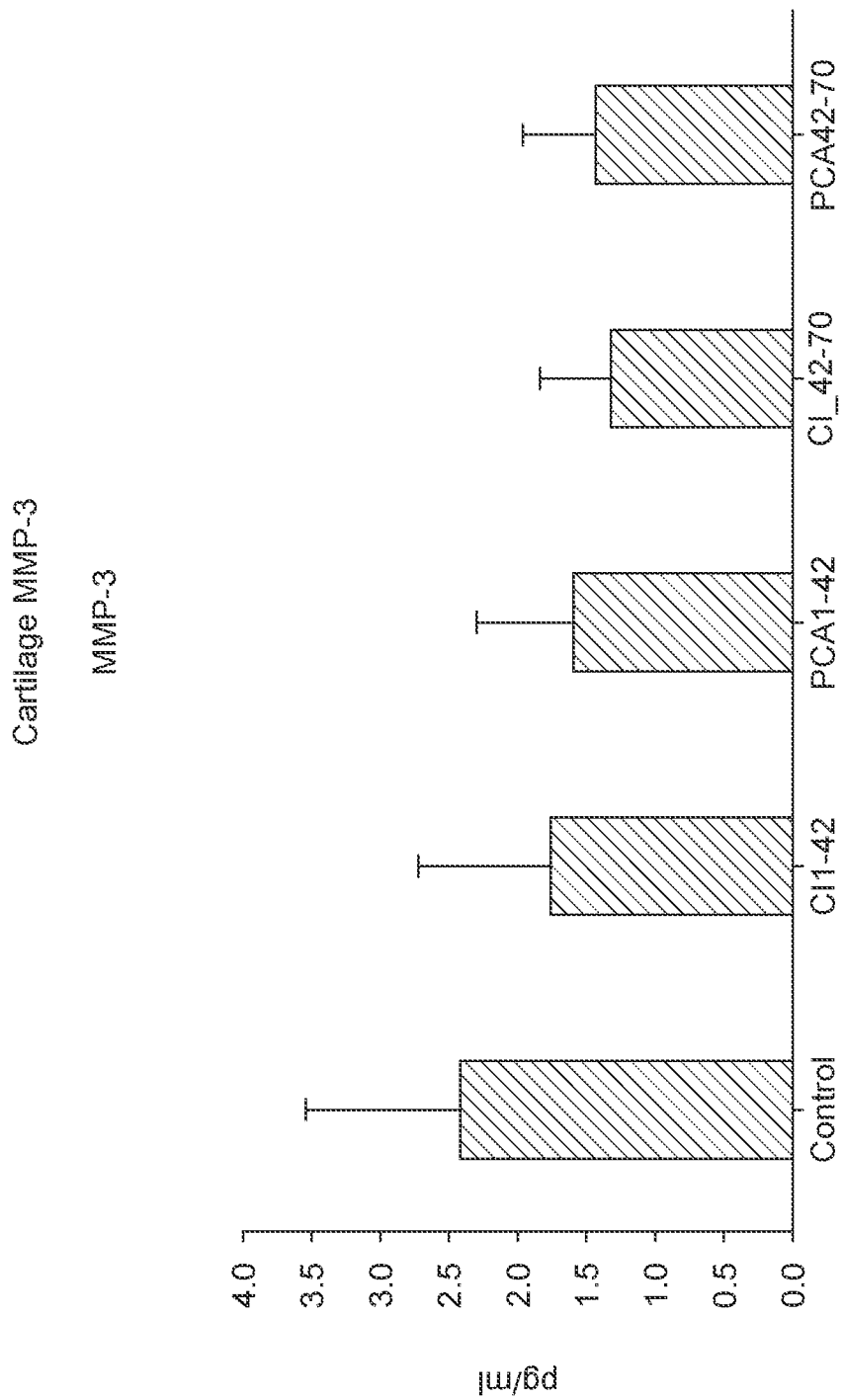
FIG. 3 shows that MMP-3 expression in cartilage was reduced in the both the therapeutic and the prophylactic G3G and PCA groups.
Figure 4:
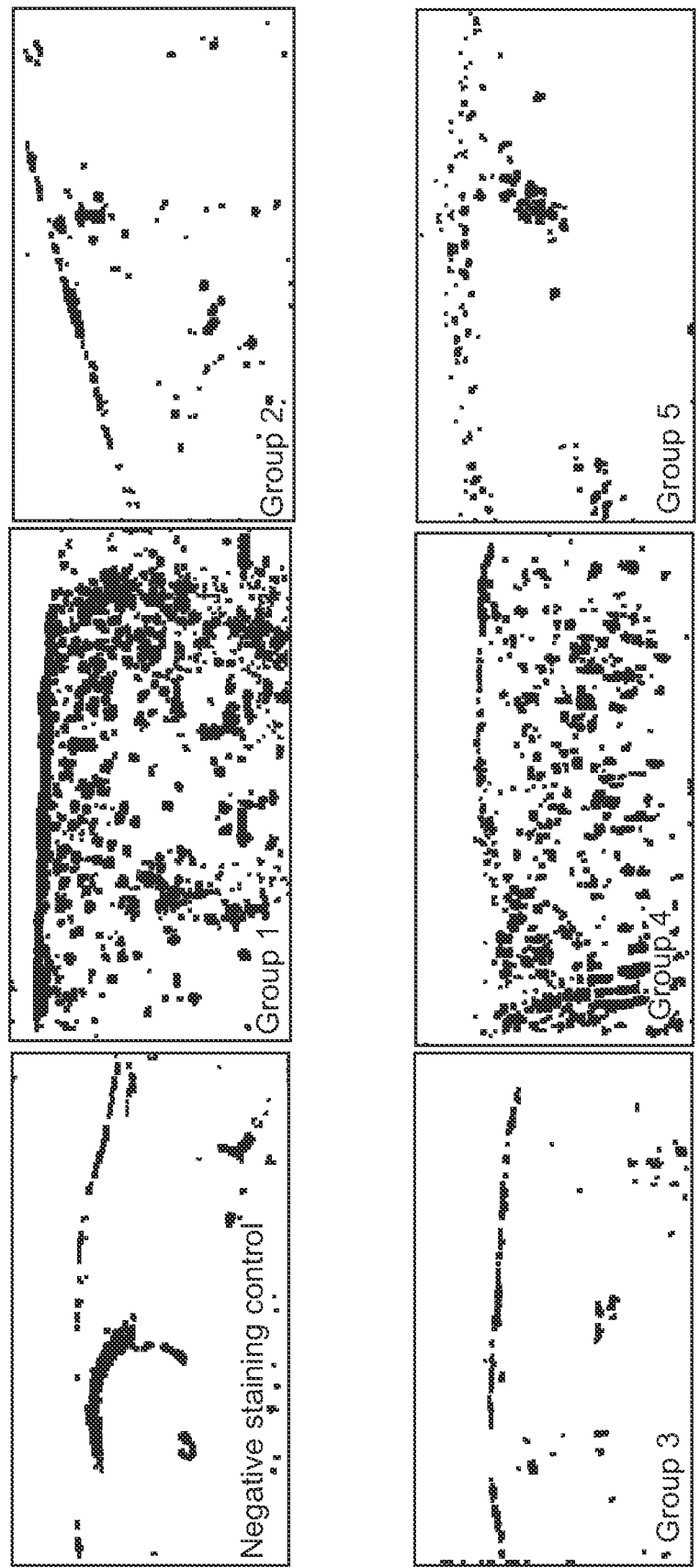
FIG. 4 provides results of histochemical staining for the presence of MMP-3 and expression in cartilage. The negative control shows no staining. Group 1 is a positive control. Group 2 (C3G prophylactic) shows very minimal positive stain for MMP3 with a single arrow pointing to the positive stain. Groups 3 (PCA prophylactic) and Group 4 (C3G therapeutic) and Group 5 (PCA therapeutic) show no staining.

MMP-3 expression in cartilage was reduced in the both the therapeutic and the prophylactic G3G and PCA groups. See FIGS. 3 and 4.

IGF-1

Insulin-like growth factor 1 (IGF-1), also called somatomedin C, is a protein plays an important role in childhood growth and continues to have anabolic effects in adults. Its primary action is mediated by binding to its specific receptor, the insulin-like growth factor 1 receptor (IGF1R), which is present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the anterior pituitary gland, is released into the blood stream, and then stimulates the liver to produce IGF-1. IGF-1 then stimulates systemic body growth, and has growth-promoting effects on almost every cell in the body, especially skeletal muscle, cartilage, bone, liver, kidney, nerves, skin, hematopoietic cell, and lungs.

IGF-1 was increased in the plasma only in the prophylactic PCA group as measured by PG/M L.

Figure 5A:
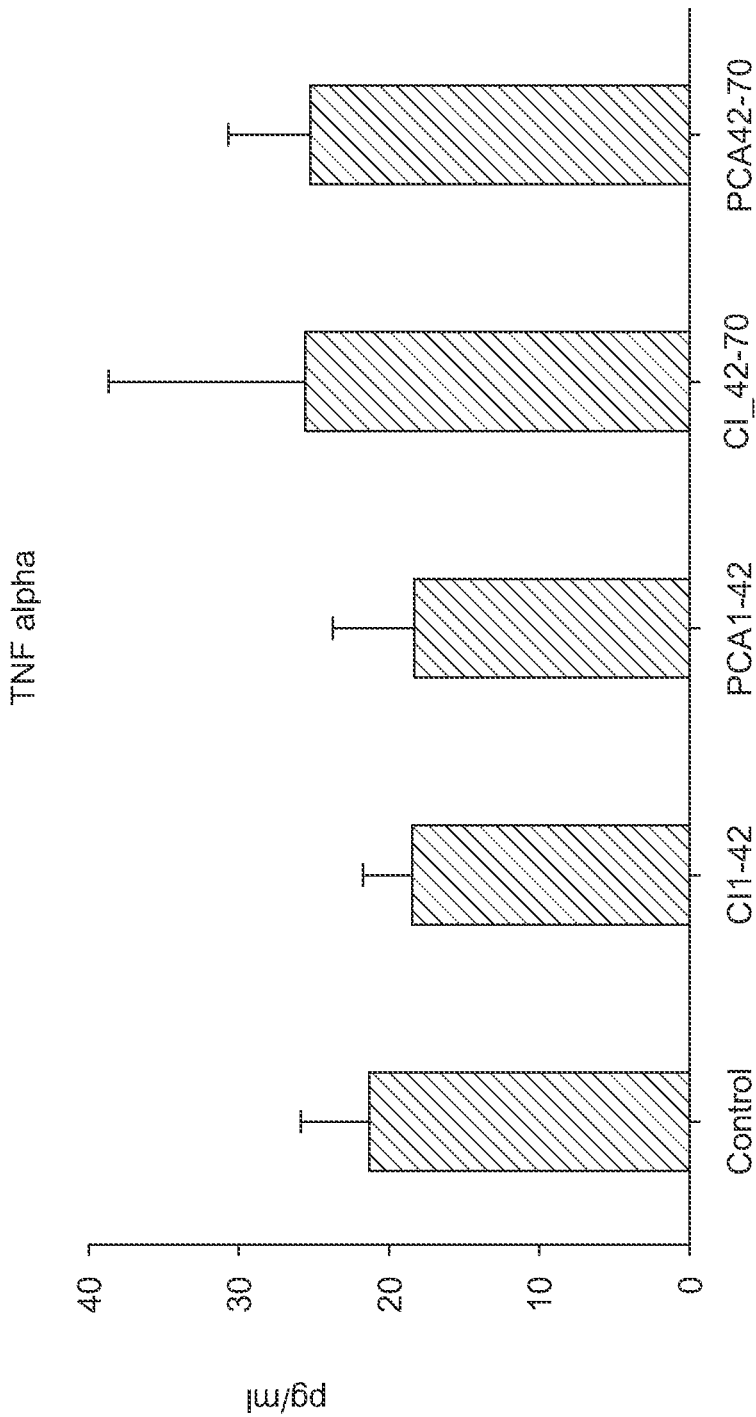
FIG. 5A shows that TNF-alpha levels showed a slight increase in the synovial fluid for the C3G and PCA therapeutic groups and a slight decrease in both of the therapeutic groups. However, the differences seen are not statistically significant. However, notably the reduction occurred due to the longer treatment time; 6 weeks in the prophylactic group as opposed to 4 weeks in the therapeutic groups. Thus, a viable therapy would preferably have a minimum 6-week duration required for depression of TNF-α.
Figure 5B:
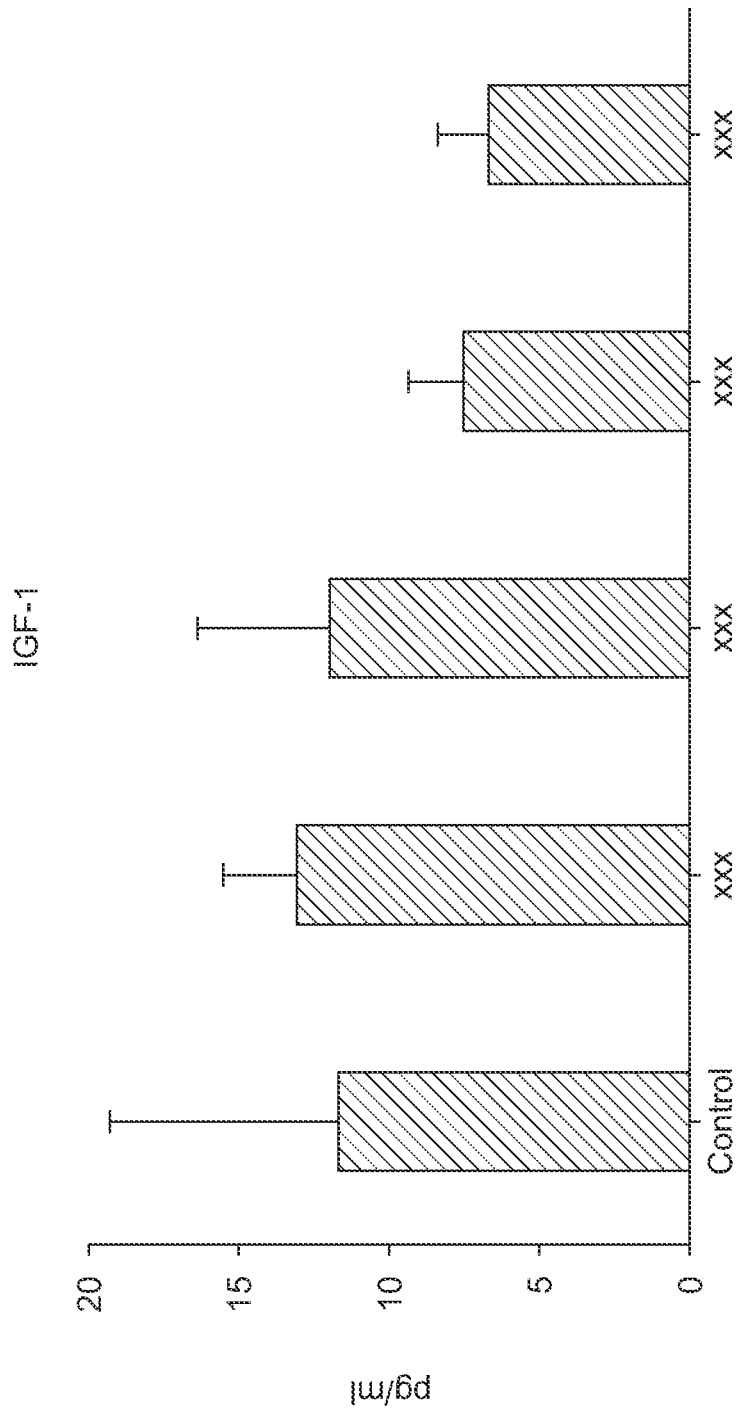
FIG. 5B shows that IFG-1 levels in the synovial fluid was not significantly changed in all groups. However, notably the levels were slightly elevated in the 6-week prophylactic group, but not the 4 week therapeutic groups. This may hint that the timing of the treatment may be important. Further the results shown in this graph also has to be balanced by the synovial fluid IGF-1 receptor amounts detected by ELISA. IGF-1 was active in preserving the patellar cartilage.

Control group: 25 PG/ML
Prophylactic C3G group: 15.8 PG/ML
Prophylactic PCA group: 43.0 PG/ML
Therapeutic C3G group: 28.5 PG/ML
Therapeutic PCA group: 29.0 PG/ML Synovial Fluid—Detected by ELISA IFG-1 was not statistically significantly changed in all groups. See FIG. 5B.

Synovial Tissue (Synovium)—Detected by ELISA

Figure 8A:
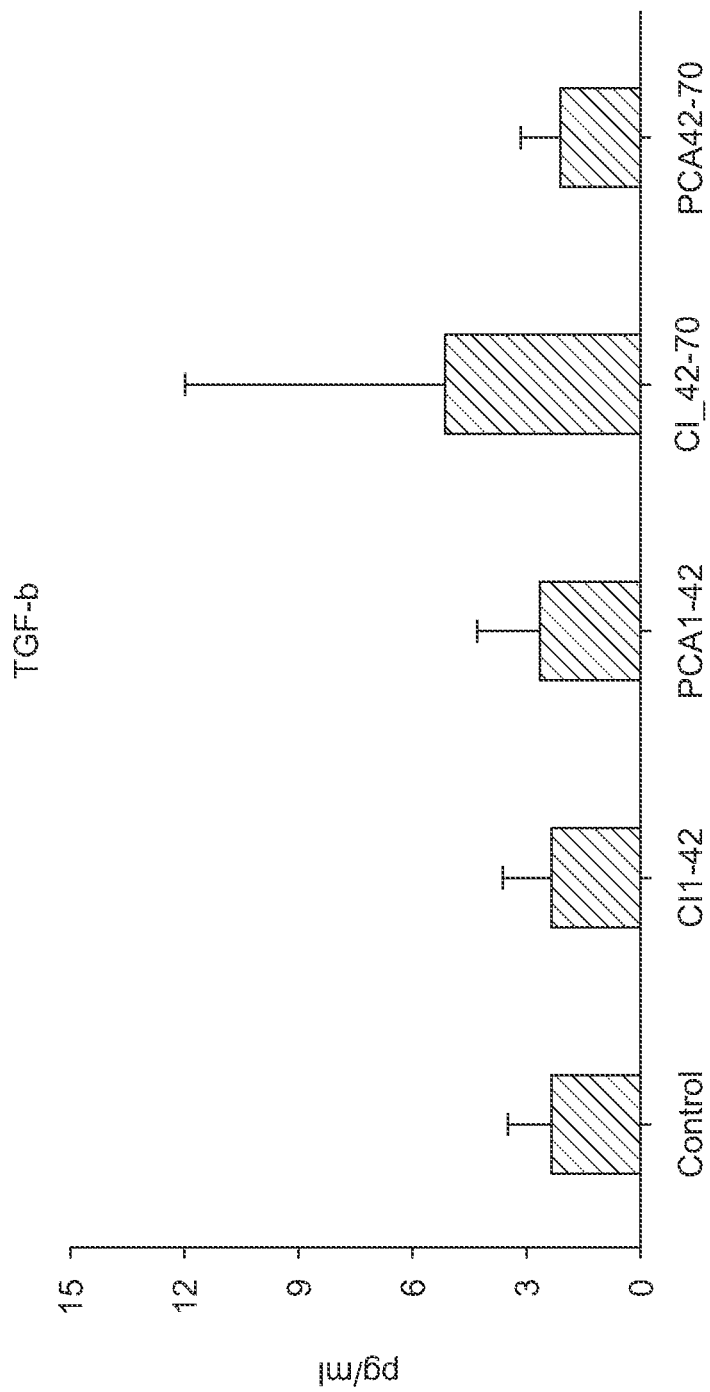
FIG. 8A shows that TGF-beta was increased in the synovium only in the C3G therapeutic group.
Figure 8B:
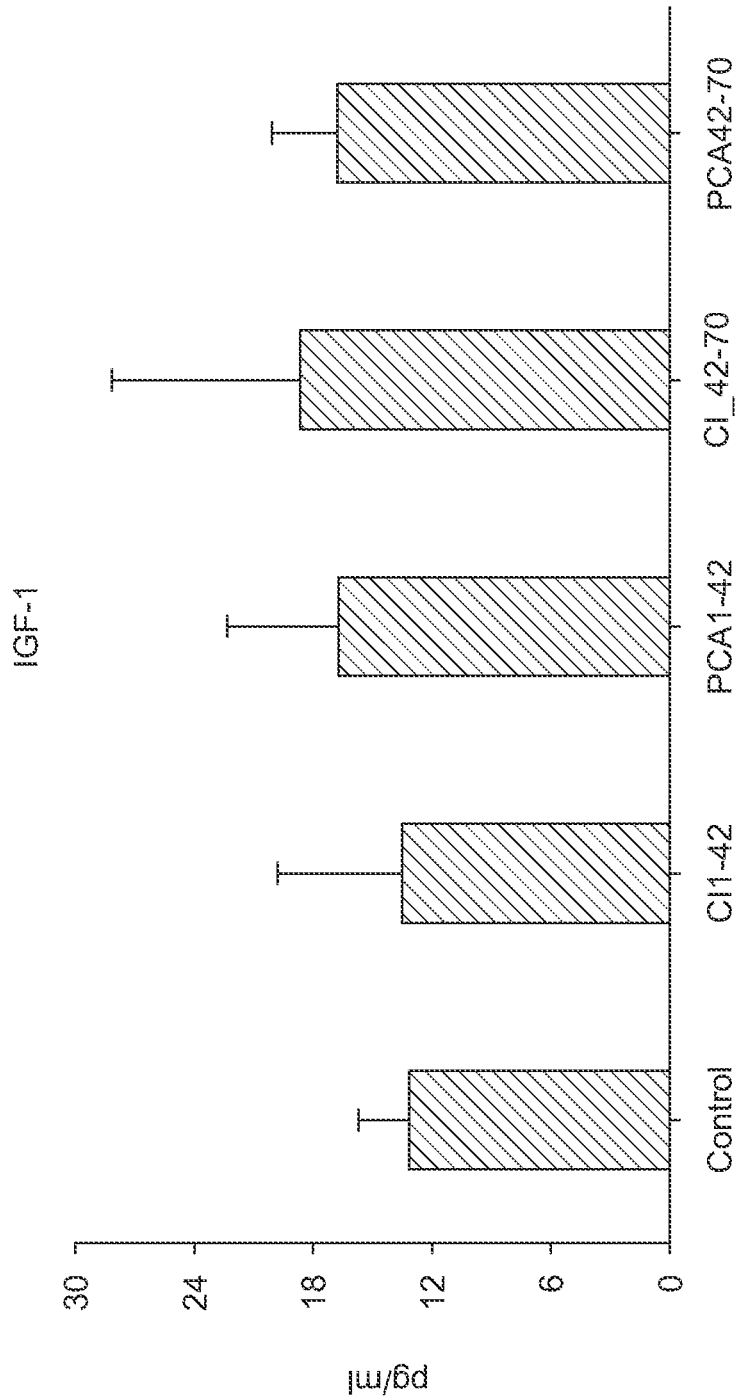
FIG. 8B shows that IGF-1 levels in the synovium was increased in all groups.

IGF-1 was increased in all groups. See FIG. 8B.

Synovial Tissue (Synovium)—Gene Expression Level Detected by Real-Time PCR

Figure 13B:
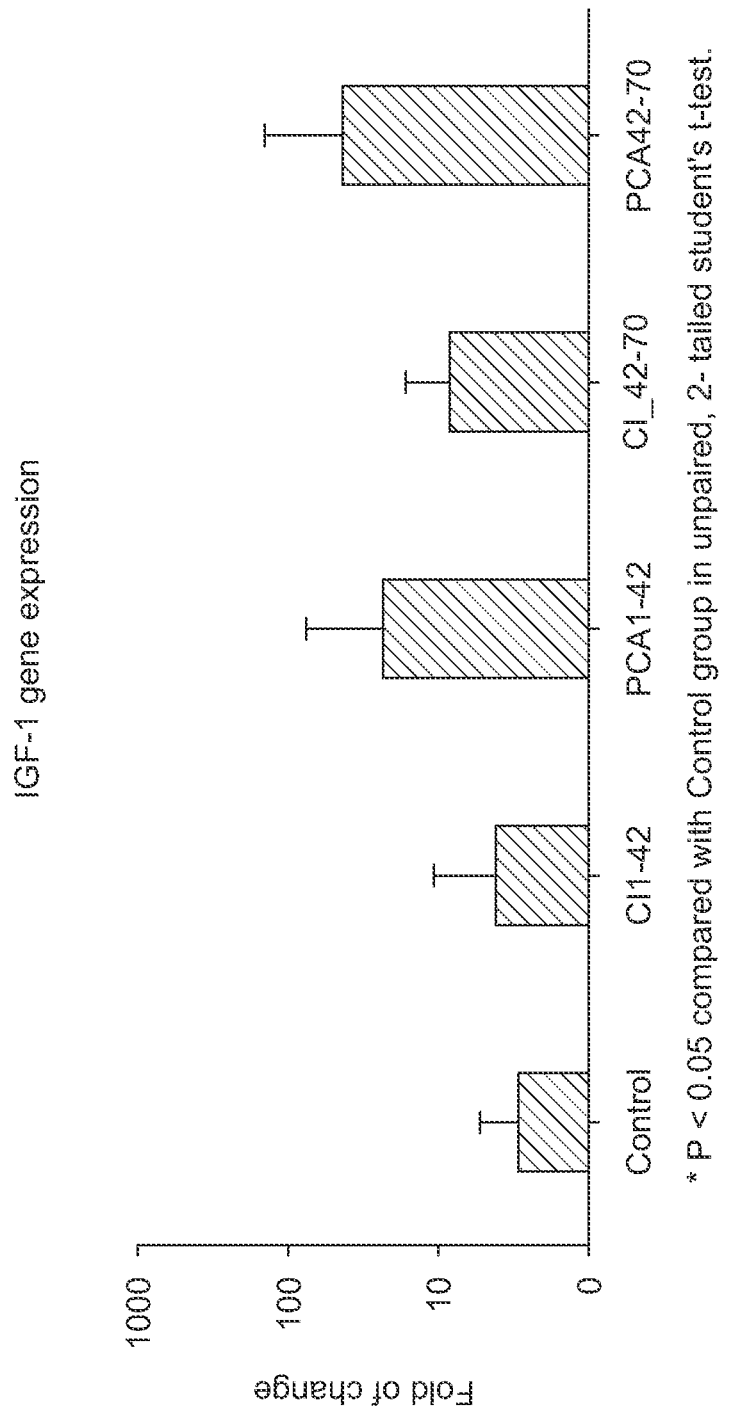
FIG. 13B shows that IGF-1 gene expression as detected by real-time PCR was increased in all groups.

IGF-1 was increased in all groups. See FIG. 13B.

MMP-1

Matrix metalloproteinase-1 (MMP-1) also known as interstitial collagenase and fibroblast collagenase is an enzyme that is involved in the breakdown of extracellular matrix in normal physiological processes, such as embryonic development, reproduction, and tissue remodeling, as well as in disease processes, such as arthritis and metastasis. Specifically, MMP-1 breaks down the interstitial collagens, types I, II, and III.

Synovial Fluid—Detected by ELISA

Figure 7:
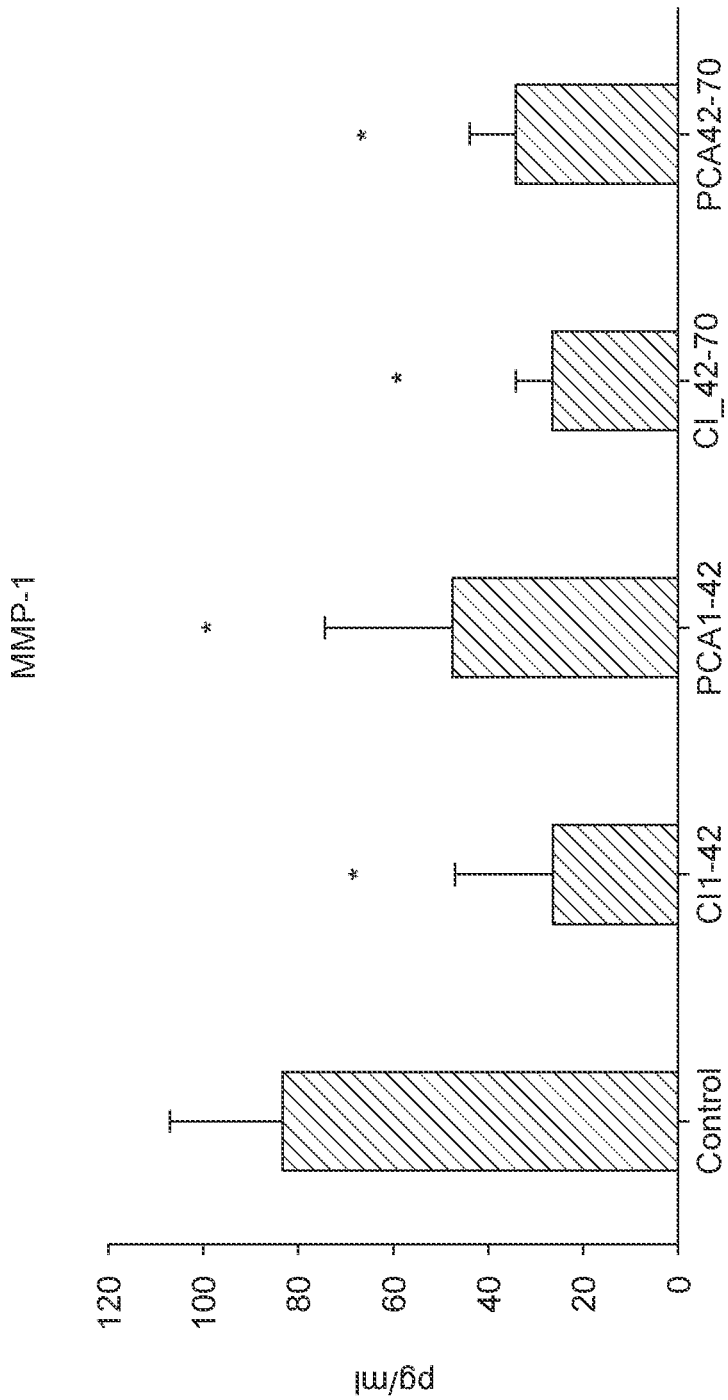
FIG. 7 shows that MMP-I levels in the synovial fluid were decreased significantly in all groups.

MMP-1 was decreased significantly in all groups. See FIG. 7.

Synovial Tissue (Synovium)—Detected by ELISA

Figure 11:
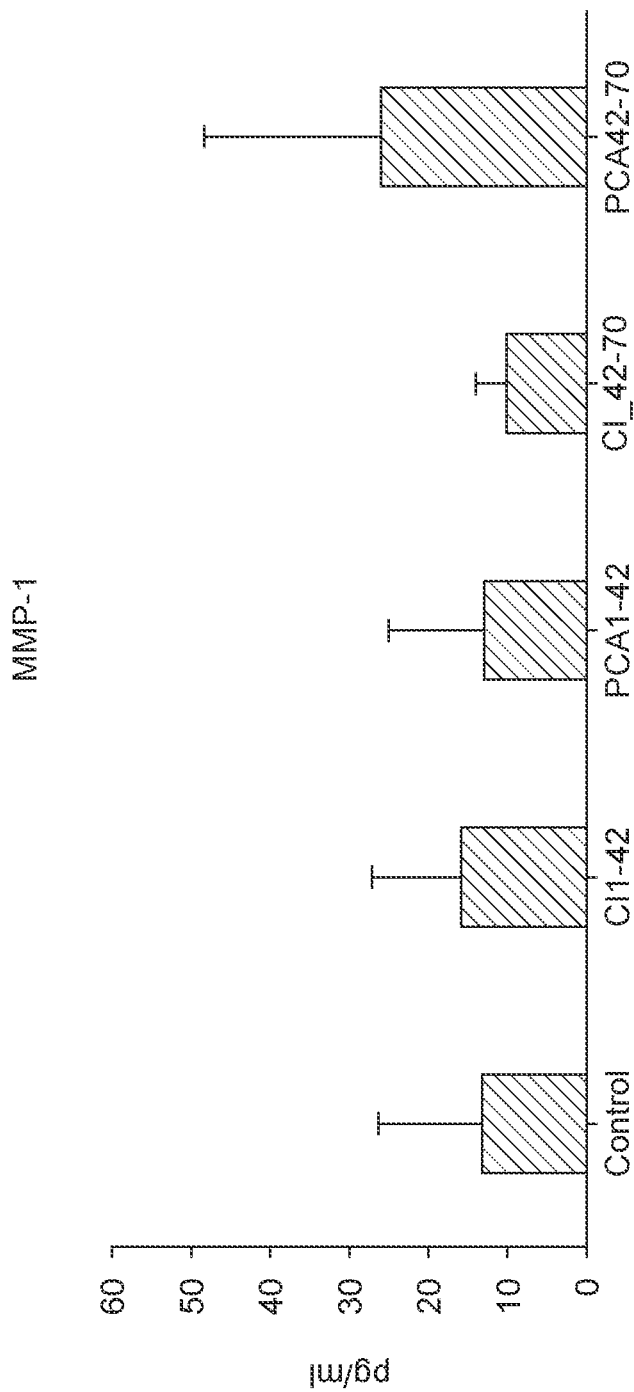
FIG. 11 shows that the therapeutic C3G group showed a decrease in MMP-1 in the synovium.

The therapeutic C3G group showed a decrease in MMP-1 in the synovium. See FIG. 11.

Il-1 Beta

Interleukin-1 beta (IL-1β) also known as catabolic, is a cytokine protein. This cytokine is an important mediator of the inflammatory response, and is involved in a variety of cellular activities, including cell proliferation, differentiation, and apoptosis. Increased production of IL-1B causes a number of different auto-inflammatory syndromes.

Synovial Fluid—Detected by ELISA

Levels of IL-1 beta were decreased in all groups. See FIG. 2A.

Synovial Tissue (Synovium)—Detected by ELISA

Levels of IL-1 beta were decreased in the C3G and PCA therapeutic groups but were increased in the two prophylactic groups. See FIG. 9A.

Expression in Cartilage

Figure 14:
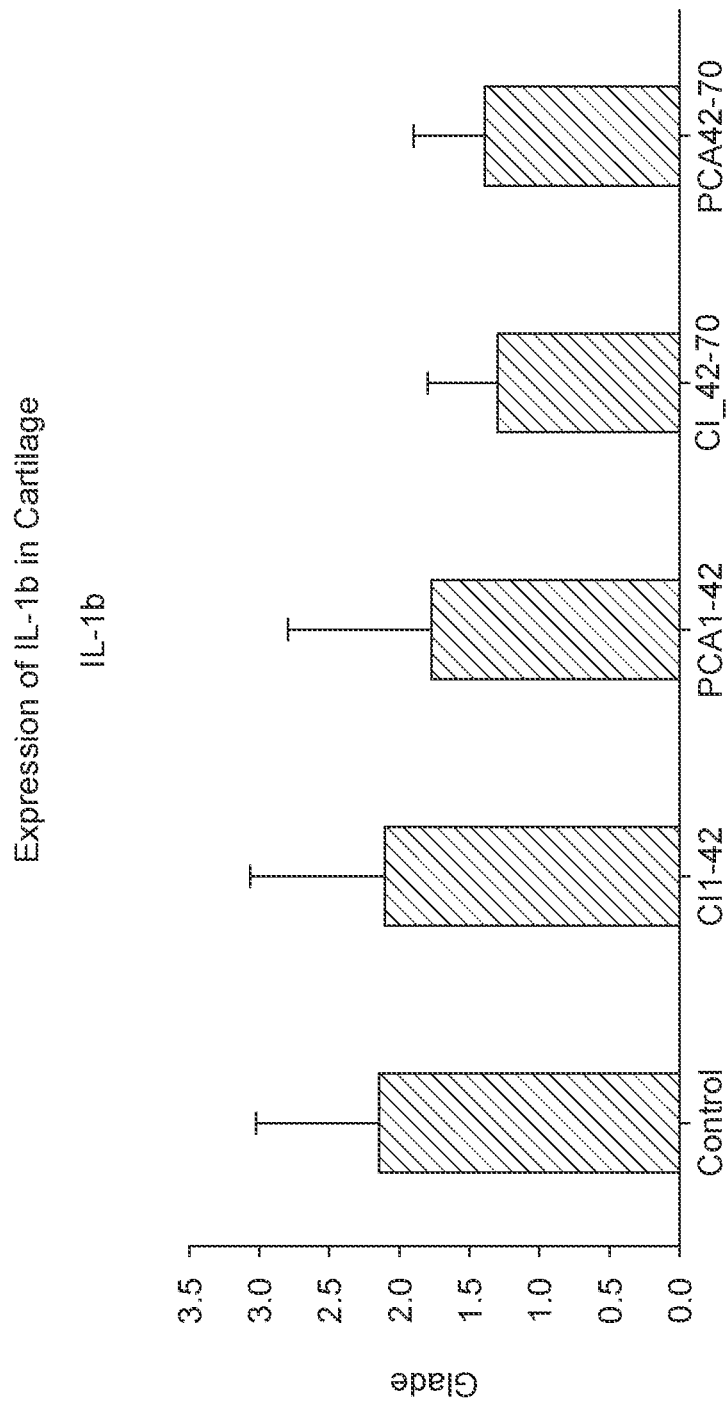
FIG. 14 shows that expression of IL-Beta in cartilage is decreased in all four groups.
Figure 15:
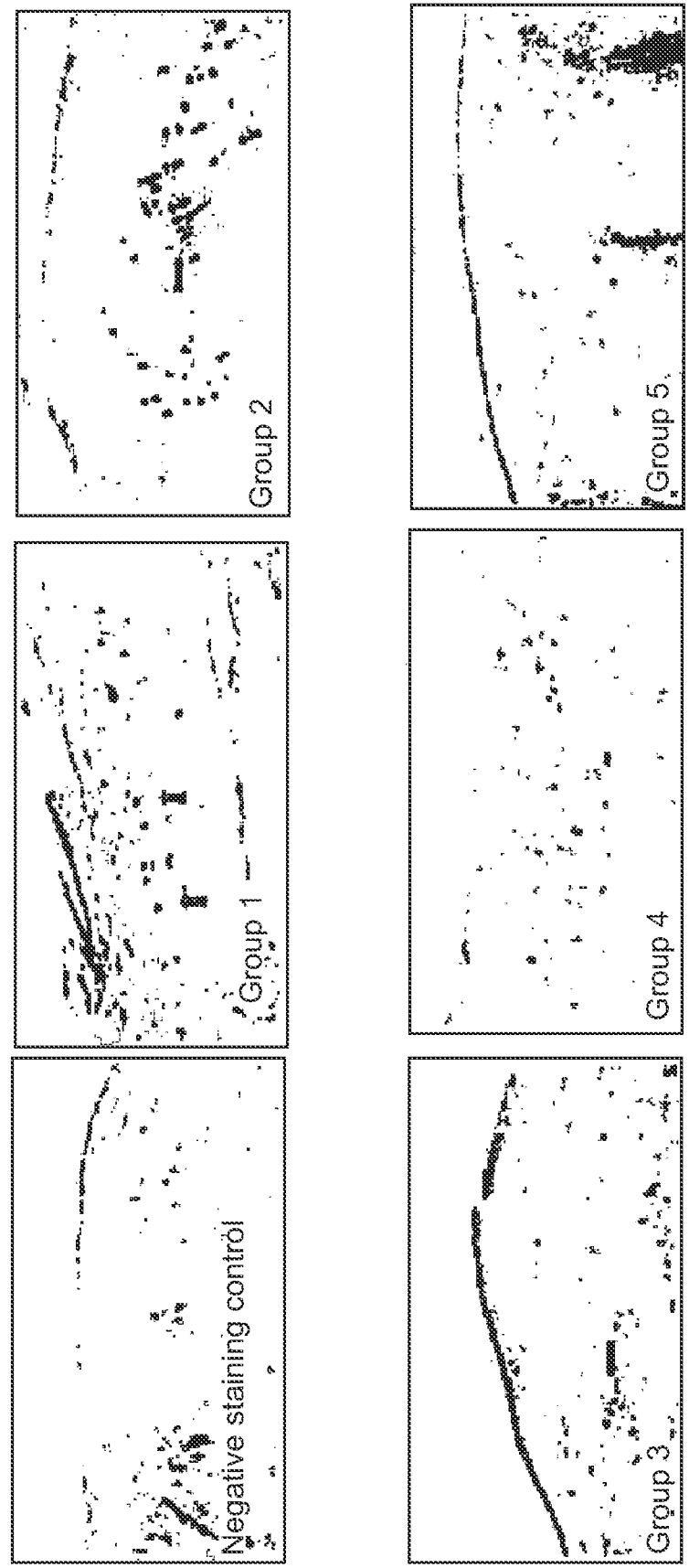
FIG. 15 shows the results of immunohistochemical staining for IL-Beta in rabbit tissue supporting FIG. 14.

FIGS. 14 and 15 show that expression of IL-Beta in cartilage is decreased in all four groups.

TGF-Beta

TGF-β induces apoptosis in numerous cell types. Transforming growth factor beta (TGF-β) is a protein that controls proliferation, cellular differentiation, and other functions in most cells. It is a type of cytokine which plays a role in immunity, cancer, bronchial asthma, heart disease, diabetes, hereditary hemorrhagic telangiectasia, Marfan syndrome, vascular Ehlers-Danlos syndrome Loeys-Dietz syndrome, Parkinson's disease, and AIDS.

Synovial Fluid—Detected by ELISA

TGF-beta was decreased in all groups. See FIG. 2B.

Synovial Tissue (Synovium)—Detected by ELISA

TGF-beta was increased in the C3G therapeutic group. See FIG. 8A.

Lubricin

Proteoglycan 4 or lubricin is a proteoglycan that acts as a joint/boundary lubricant. Lubricin is present in synovial fluid and on the surface (superficial layer) of articular cartilage and therefore plays an important role in joint lubrication and synovial homeostasis.

Exposure of synoviocytes, chondrocytes and cartilage explants to proinflammatory cytokines such as Il-1 and TNF-alpha results in a marked reduction in the expression and/or abundance of secreted lubricin, with corresponding alterations in the amounts of cartilage-associated lubricin. Jones A R C, et al., European Cells and Materials Vol. 13, 2007 (pages 40-45) 2007.

Studies have shown that IL-1 inhibits the presence of lubricin and IGF-1 increases it synthesis. Flannery, C R, et al., Biochemical and Biophysical Research Communications. Vol. 254, Issue 3, 27 Jan. 1999, pages 535-541.

Synovial Tissue (Synovium)—Detected by ELISA

Figure 8C:
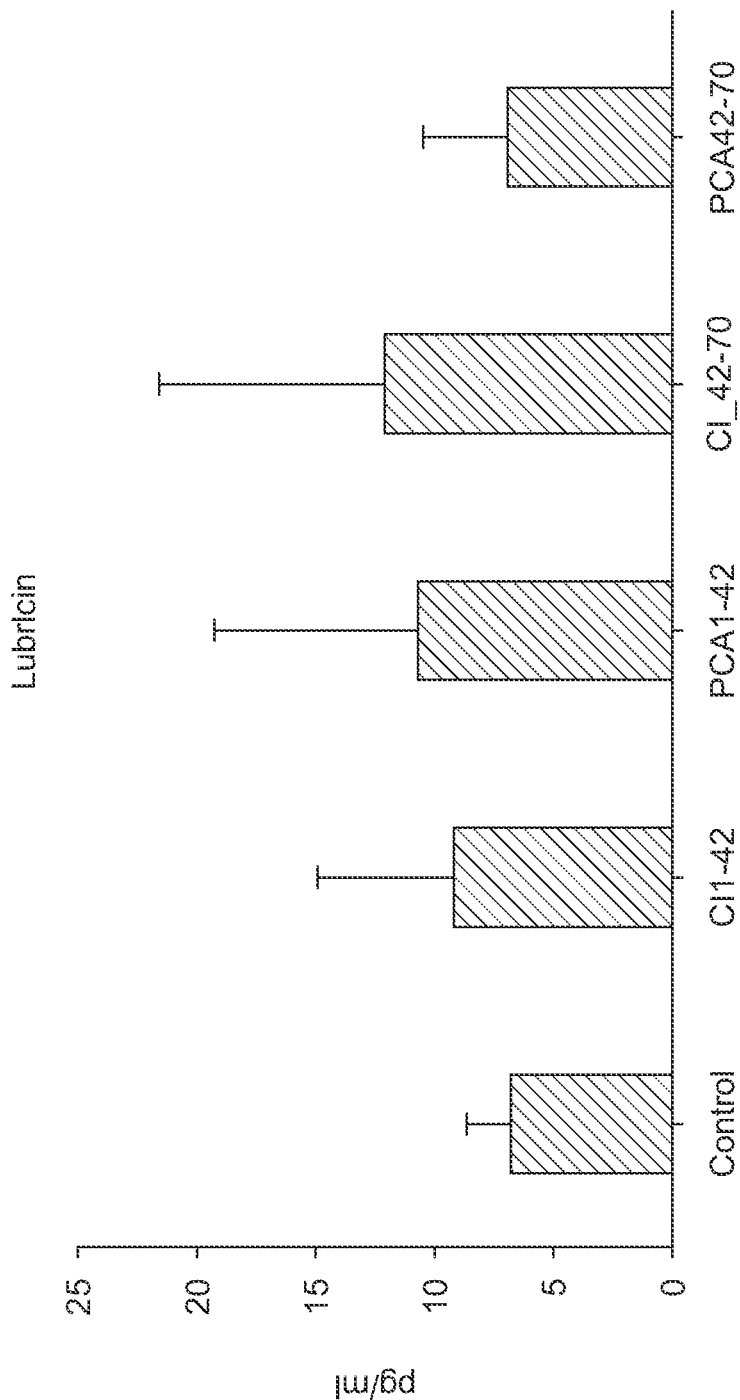
FIG. 8C shows that lubricin was increased in 3 of the 4 groups in the synovium (increase in both C3G groups and increase in the prophylactic PCA group).

Lubricin was increased in 3 of the 4 groups in the synovium (increase in both C3G groups and increase in the prophylactic PCA group). (See FIG. 8C).

Expression in Cartilage

Figure 18:
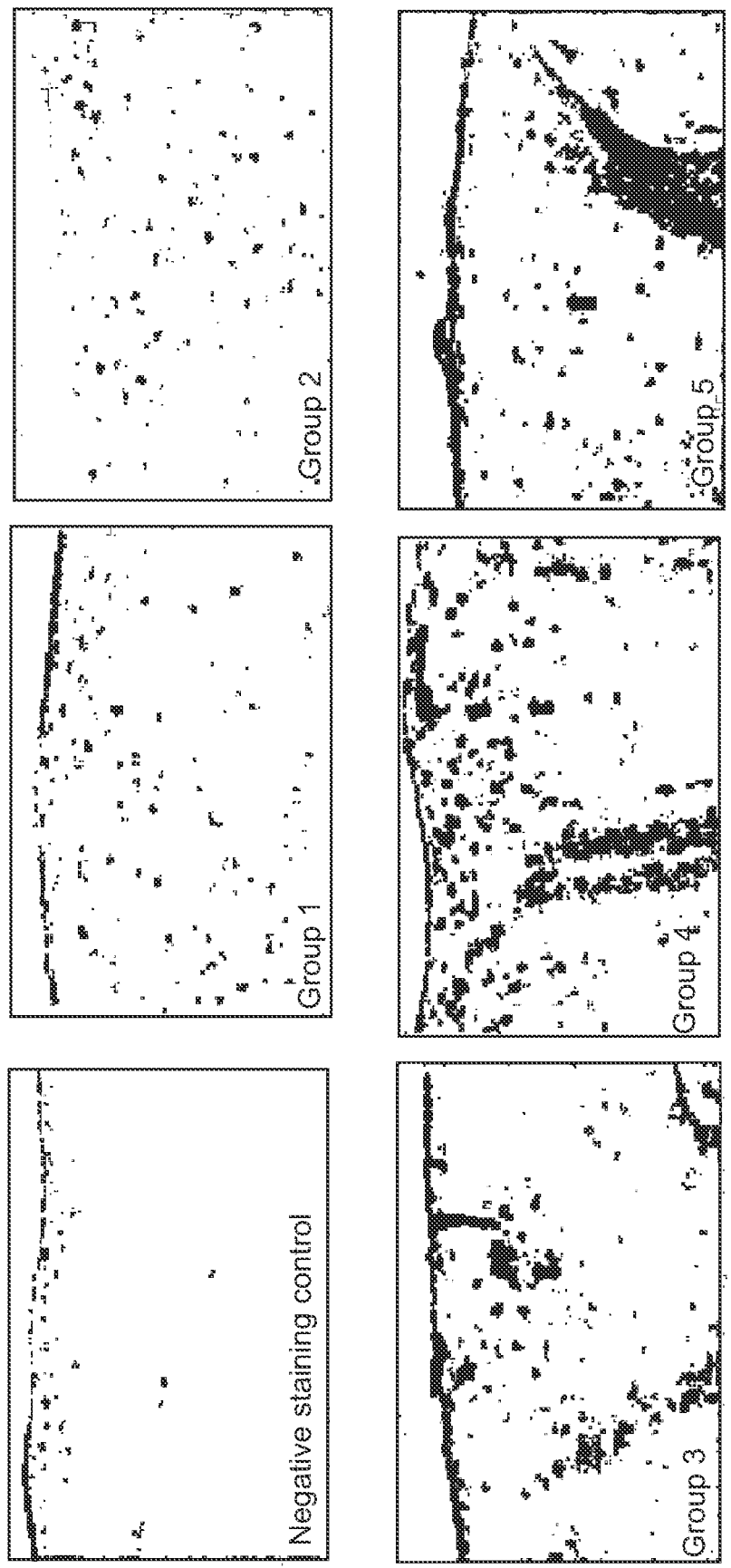
FIG. 18 provides the underlying immunohistochemical staining supporting FIG. 19.
Figure 19:
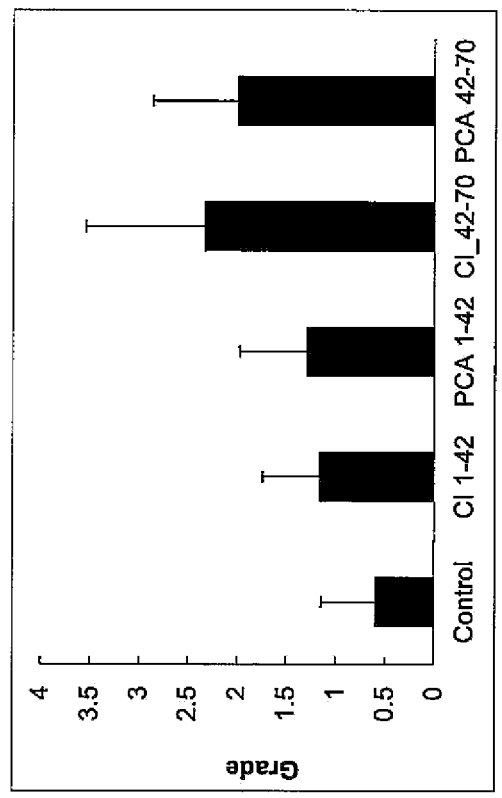
FIG. 19 shows that lubricin expression was increased in the cartilage of all four groups.

FIGS. 18 and 19 show that lubricin expression was increased in the cartilage of all four groups.

Il-6

Interleukin 6 (IL-6) is an interleukin that acts as both a pro-inflammatory cytokine and an anti-inflammatory myokine. IL-6 is secreted by T cells and macrophages to stimulate immune response, e.g. during infection and after trauma, especially burns or other tissue damage leading to inflammation. In addition, osteoblasts secrete IL-6 to stimulate osteoclast formation. IL-6's role as an anti-inflammatory cytokine is mediated through its inhibitory effects on TNF-alpha and IL-1, and activation of IL-1ra and IL-10. IL-6 is an important mediator of fever and of the acute phase response.

Synovial Tissue (Synovium)—Detected by ELISA

Il-6 was decreased in all groups. See FIG. 9C.

TNF-Alpha

Tumor necrosis factor (TNF, cachexin, or cachectin, and formerly known as tumor necrosis factor alpha or TNFα) is an adipokine involved in systemic inflammation and is a member of a group of cytokines that stimulate the acute phase reaction. It is produced chiefly by activated macrophages, although it can be produced by many other cell types such as CD4+ lymphocytes, NK cells, neutrophils, mast cells, eosinophils, and neurons. The primary role of TNF is in the regulation of immune cells. TNF, being an endogenous pyrogen, is able to induce fever, apoptotic cell death, cachexia, inflammation and to inhibit tumorigenesis and viral replication and respond to sepsis via IL1 and IL6 producing cells.

TNF promotes the inflammatory response, which, in turn, causes many of the clinical problems associated with autoimmune disorders such as rheumatoid arthritis, ankylosing spondylitis, inflammatory bowel disease, psoriasis, hidradenitis suppurativa and refractory asthma.

TNF and Il-1 are considered master cytokines in chronic, destructive arthritis. In fact, therapeutic approaches to rheumatoid arthritis (RA) is mainly focuses on TNF. Analysis of cytokine patterns in early synovial biopsy specimens of RA patients reveals prominent TNF staining in 50% of the patients, whereas IL-1beta staining was evident in 100% of the patients. Van den Berg W B., Ann Rheum Dis., November 2000; 59 (Supp 1); i81-i84.

Synovial Fluid—Detected by ELISA

TNF-alpha levels showed a slight decrease in both of the prophylactic groups. See FIG. 5A.

Synovial Tissue (Synovium)—detected by ELISA

Figure 9D:
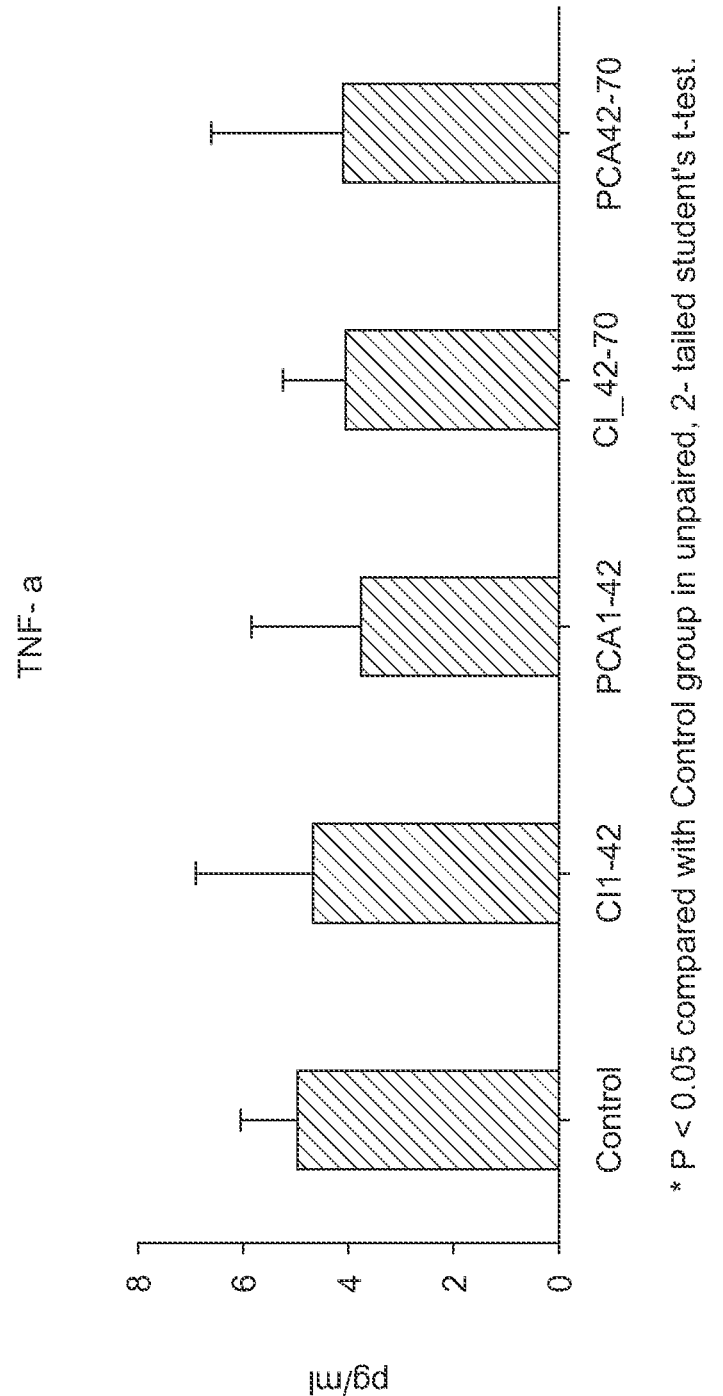
FIG. 9D shows that TNF-alpha levels were decreased in the synovium for all groups.

TNF-alpha levels were decreased in all groups. See FIG. 9D.

ADAMTS-5

ADAMTS-5 is a disintegrin and metalloproteinase with thrombospondin motifs. ADAMTS5 is a member of the ADAMTS protein family. Members of the family share several distinct protein modules, including a propeptide region, a metalloproteinase domain, a disintegrin-like domain, and a thrombospondin type 1 (TS) motif. Individual members of this family differ in the number of C-terminal TS motifs, and some have unique C-terminal domains. The enzyme encoded by this gene contains two C-terminal TS motifs and functions as aggrecanase to cleave aggrecan, which is a critical component of cartilage and joints. Thus ADAMTS-5 has a catabolic effect on cartilage.

Synovial Fluid—Detected by ELISA

Figure 6B:
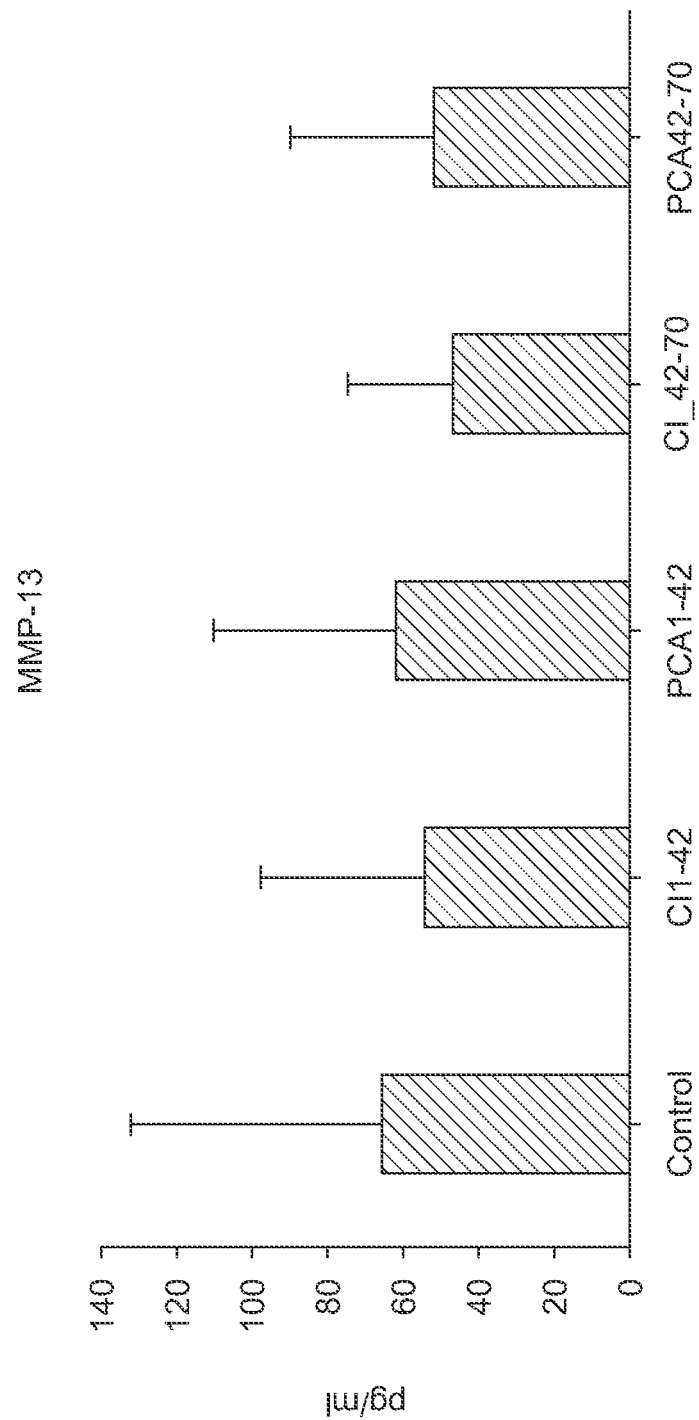
FIG. 6B shows that MMP-13 was decreased in the synovial fluid for all groups.

ADAMTS-5 was decreased in both C3G groups and an in the therapeutic PCA group. See FIG. 6A.

Synovial Tissue (Synovium)—Gene Expression Level Detected by Real-Time PCR

Figure 12:
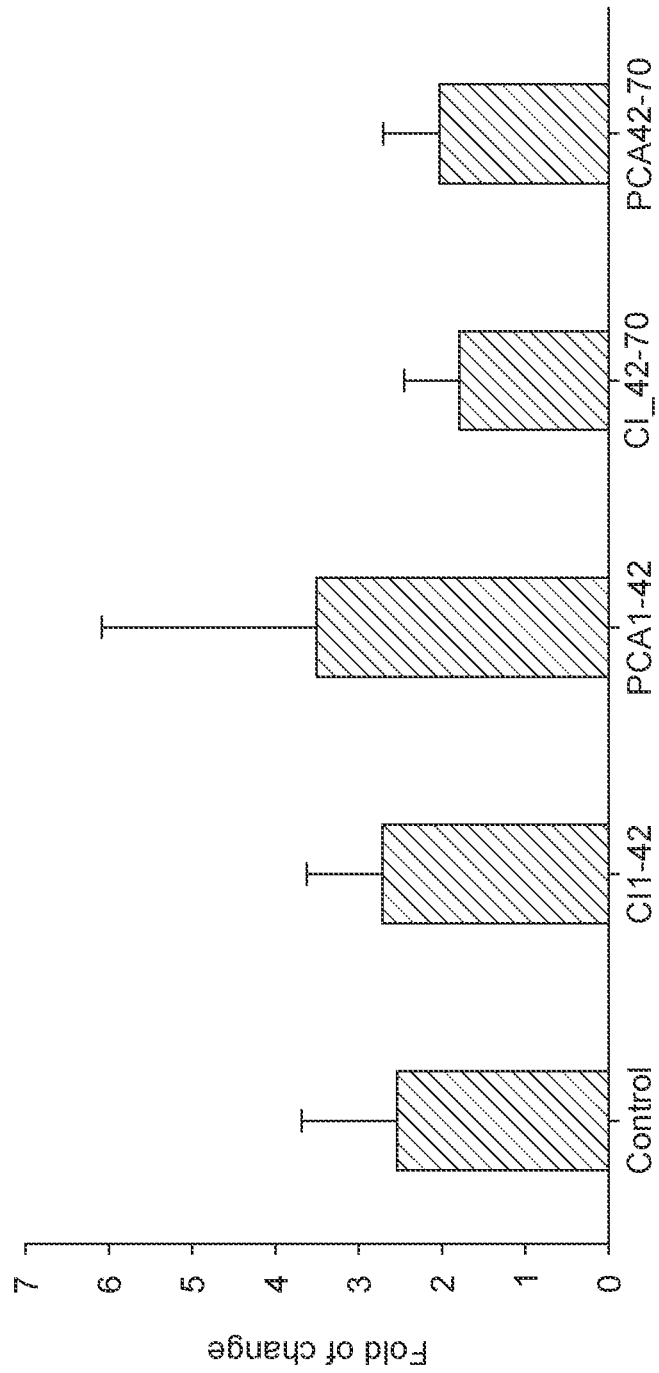
FIG. 12 shows that ADAMTS-5 gene expression was decreased in the synovium in the C3G and the PCA therapeutic groups.

ADAMTS-5 gene expression was decreased in the synovium in the C3G and the PCA therapeutic groups. See FIG. 12.

MMP-13

MMP-13 is also known as collagenase 3 and is an enzyme and a member of the matrix metalloproteinase (MMP) family. During embryonic development, MMP13 is expressed in the skeleton as required for restructuring the collagen matrix for bone mineralization. In pathological situations it is highly overexpressed; this occurs in human carcinomas, rheumatoid arthritis, and osteoarthritis. Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. The protein encoded by this gene cleaves type II collagen more efficiently than types I and III. It may be involved in articular cartilage turnover and cartilage pathophysiology associated with osteoarthritis.

Synovial Fluid—Detected by ELISA

MMP-13 was decreased in all groups. See FIG. 6B.

Synovial Tissue (Synovium)—Detected by ELISA

Figure 1:
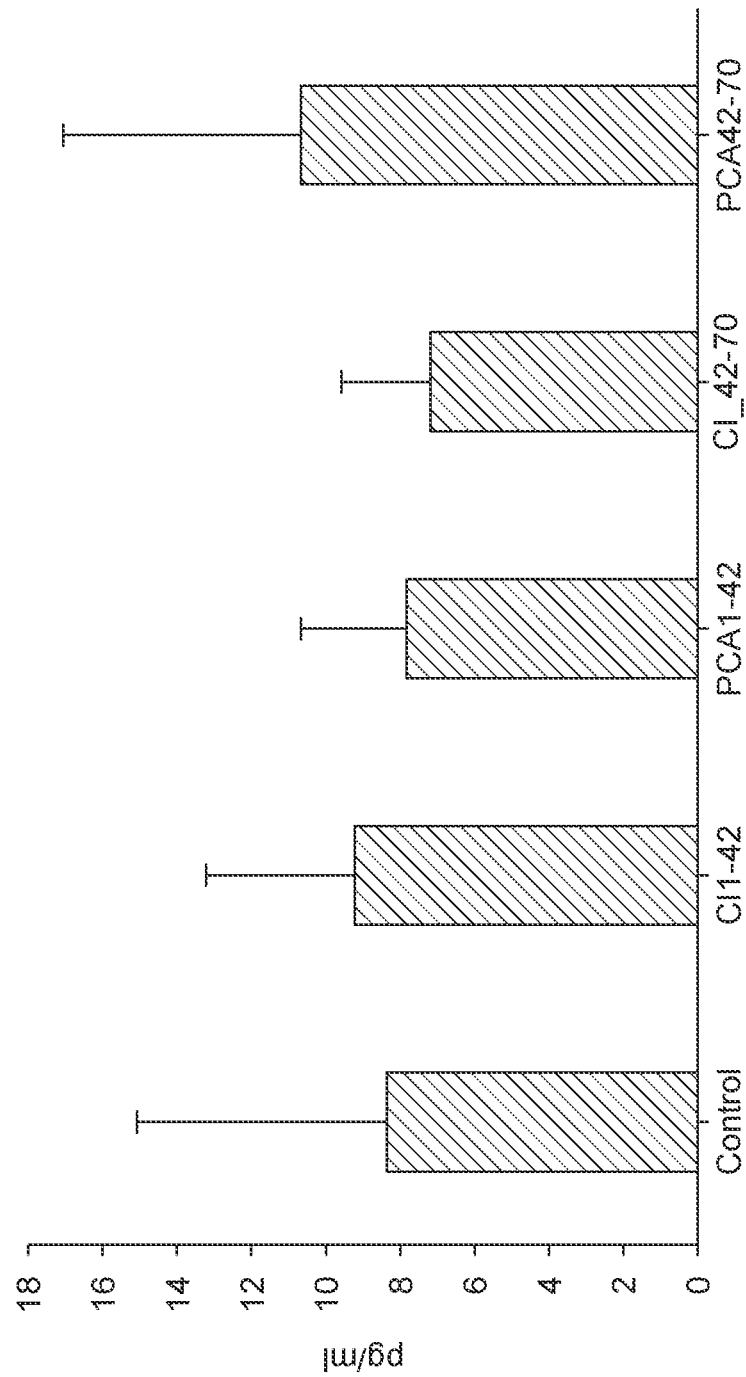
FIG. 1 (synovium) shows that MMP-13 levels were slightly decreased in the C3G therapeutic group and very slightly decreased in the PCA prophylactic group. The levels seemed to be increased slightly in the PCA therapeutic and the C3G prophylactic group. However, the levels of change appear not to be statistically significant.

MMP-13 levels were slightly decreased in the C3G therapeutic group and very slightly decreased in the PCA prophylactic group. The levels seemed to be increased slightly in the PCA therapeutic and the C3G prophylactic group, but this is not a statistical significant change. See FIG. 1.

TIMP-1

TIMP metallopeptidase inhibitor 1, also known as TIMP1, and is a tissue inhibitor of metalloproteinases. It is a glycoprotein that is expressed from the several tissues of organisms. This glycoprotein is a natural inhibitor of the matrix metalloproteinases (MMPs), a group of peptidases involved in degradation of the extracellular matrix. In addition to its inhibitory role against most of the known MMPs, the encoded protein is able to promote cell proliferation in a wide range of cell types and may also have an anti-apoptotic function.

Synovial Fluid—Detected by ELISA

Figure 6C:
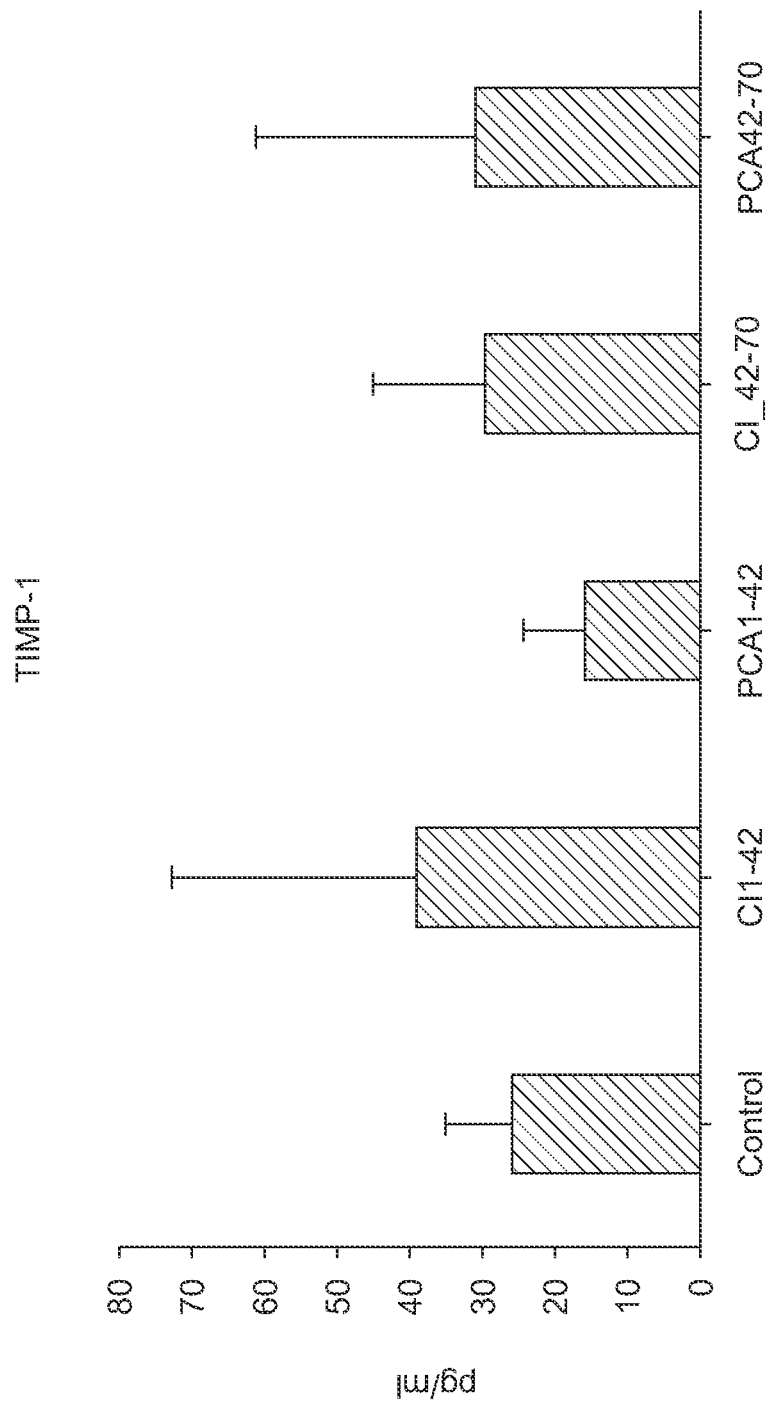
FIG. 6C shows that the TIMP-1 levels were elevated in both C3G groups and lowered in the PCA therapeutic group. However, statistical significance was not evident.

The levels were elevated in both C3G groups and in the PCA therapeutic group. See FIG. 6C.

Synovial Tissue (Synovium)—Gene Expression Level Detected by Real-Time PCR

Figure 10:
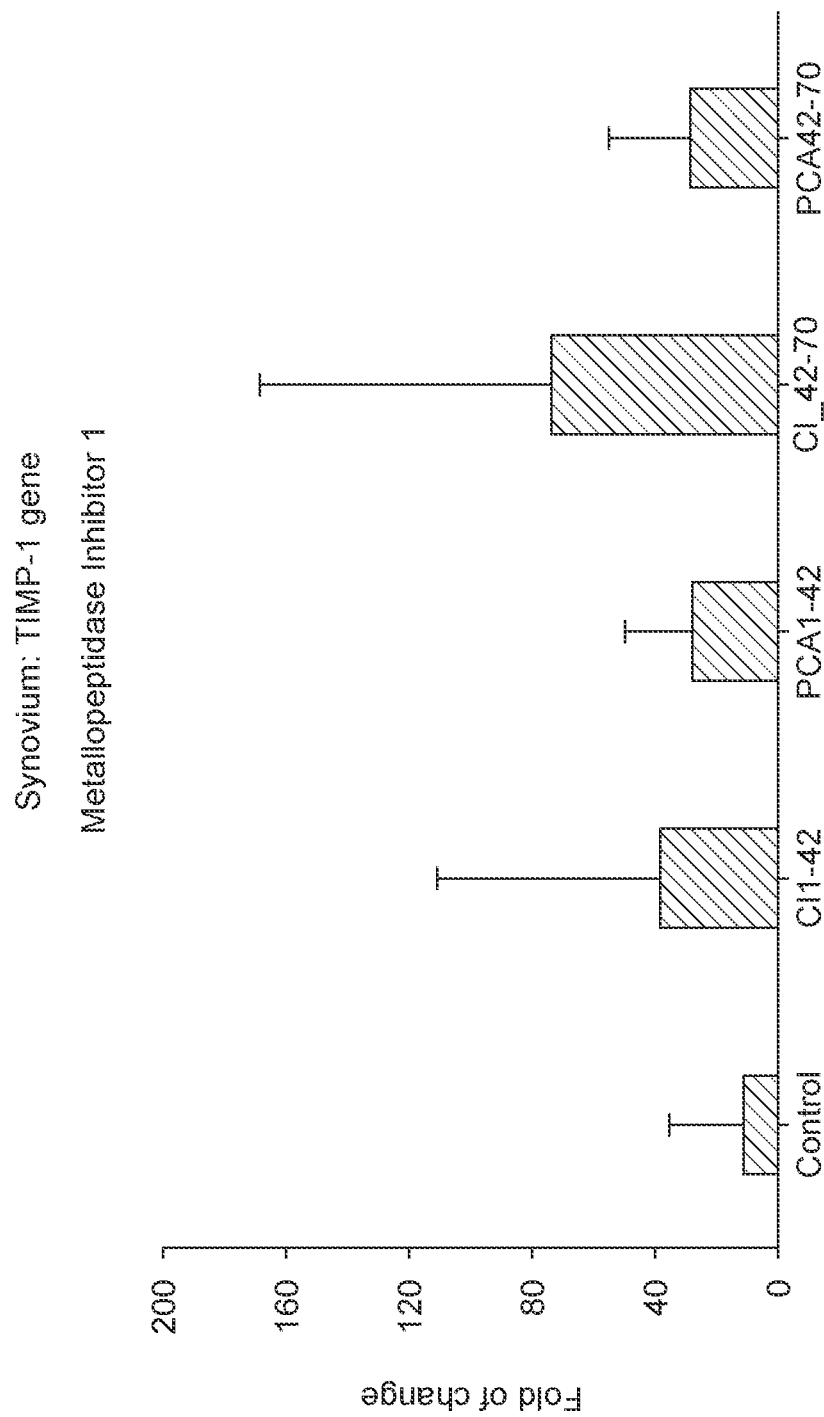
FIG. 10 shows that TIMP-1 gene expression was increased in the synovium in all four test groups.

There was an increase in gene expression in the synovium in all four test groups. See FIG. 10.

VEGF

VEGF is vascular endothelial growth factor that causes neovascularization and stops apoptosis of synovial cells.

Synovium—Detected by ELISA

The levels of VEGF were increased in all four groups. See FIG. 27.

IL-10

Interleukin-10 (IL-10), also known as human cytokine synthesis inhibitory factor (CSIF), is an anti-inflammatory cytokine. IL-10 is capable of inhibiting synthesis of pro-inflammatory cytokines such as IFN-γ, IL-2, IL-3, TNFα and GM-CSF made by cells such as macrophages and regulatory T-cells. It also displays a potent ability to suppress the antigen-presentation capacity of antigen presenting cells.

Synovial Fluid—Detected by ELISA

Levels of IL-10 were increased in all four groups. See FIG. 28.

Il-4

The presence of IL-4 in extravascular tissues promotes alternative activation of macrophages into M2 cells and inhibits classical activation of macrophages into M1 cells. An increase in repair macrophages (M2) is coupled with secretion of IL-10 and TGF-6 that result in a diminution of pathological inflammation.

Synovial Fluid—Detected by ELISA

All four groups showed an increase in IL-4. See FIG. 29.

Collagen II

Collagen II is the bases for articular cartilage and hyaline cartilage. It makes up 50% of all protein in cartilage and 85-905 of the collagen of articular cartilage.

Figure 16:
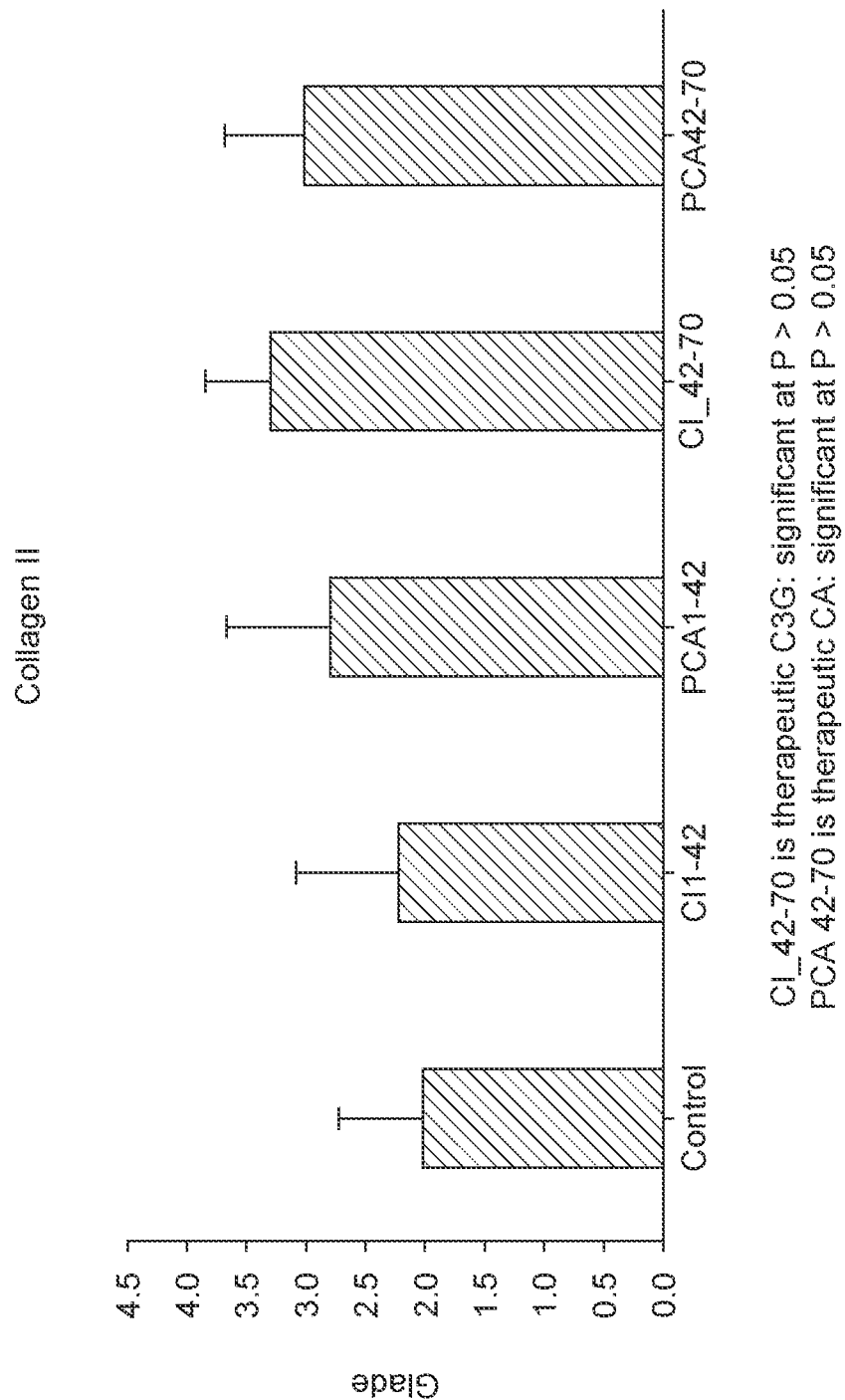
FIG. 16 shows that collagen II expression in cartilage is increased in all 4 groups.
Figure 17:
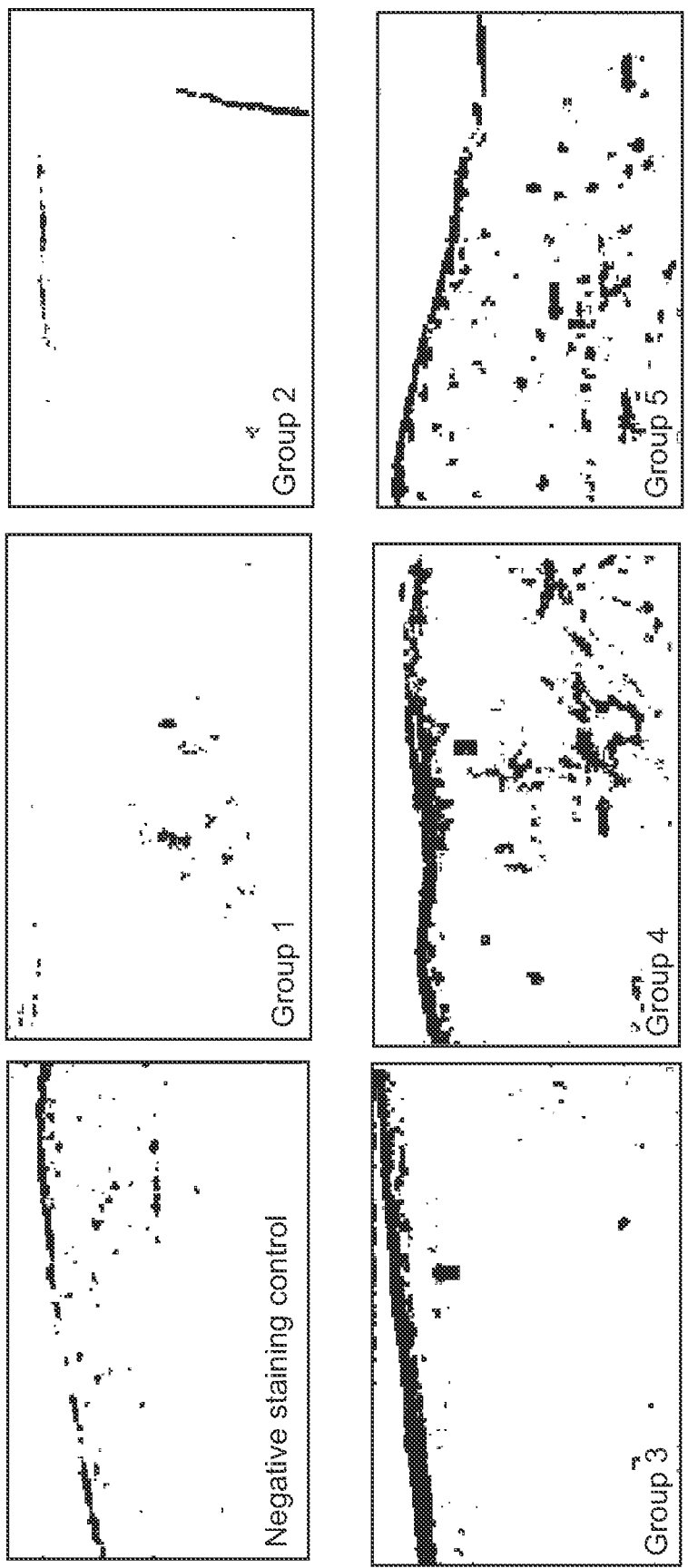
FIG. 17 provides the underlying immunohistochemical staining supporting FIG. 16.

FIGS. 16 and 17 show that collagen II expression in cartilage is increased in all 4 groups.

Aggrecan

Aggrecan is a major component of cartilage extracellular matrix, and it imparts compressive resistance to the tissue.

Figure 20:
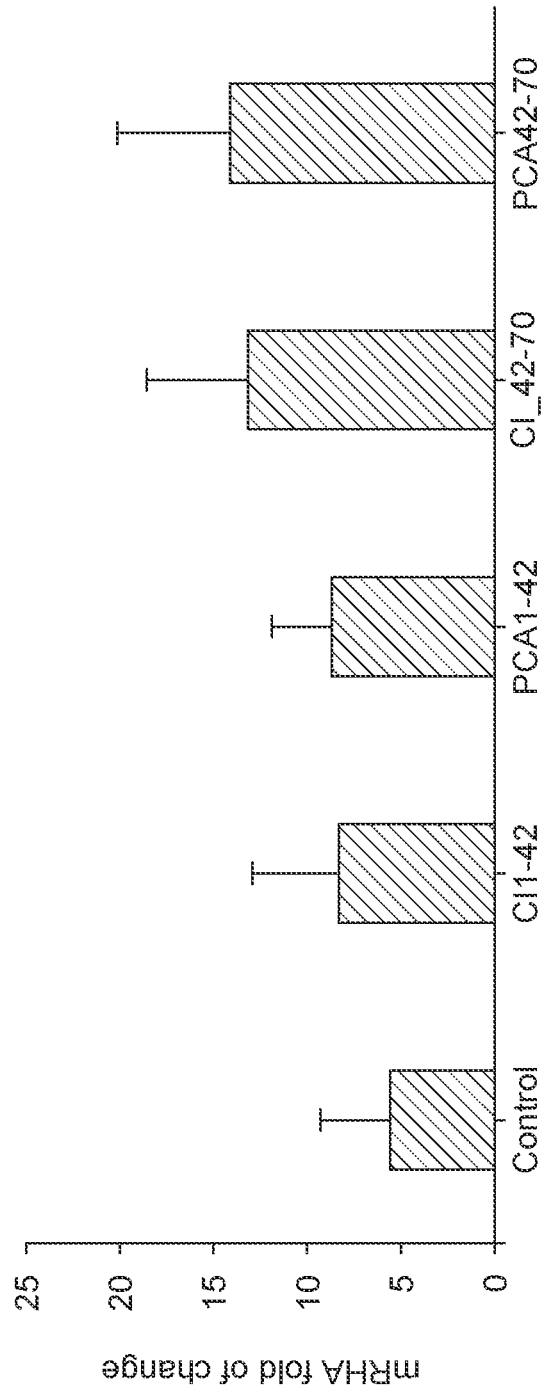
FIG. 20 shows increased expression of aggrecan in patellar cartilage of all four groups.
Figure 21:
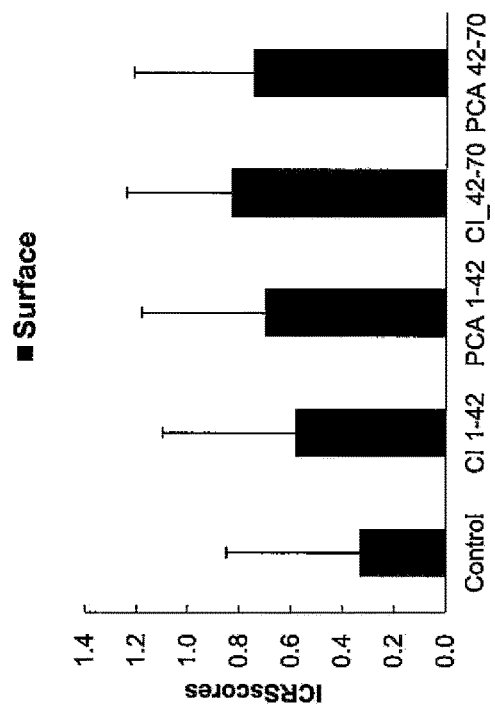
FIG. 21 provides a graph of ICRS histological visual scale scores for the surface of the cartilage. Scores for all four groups improved.
Figure 22:
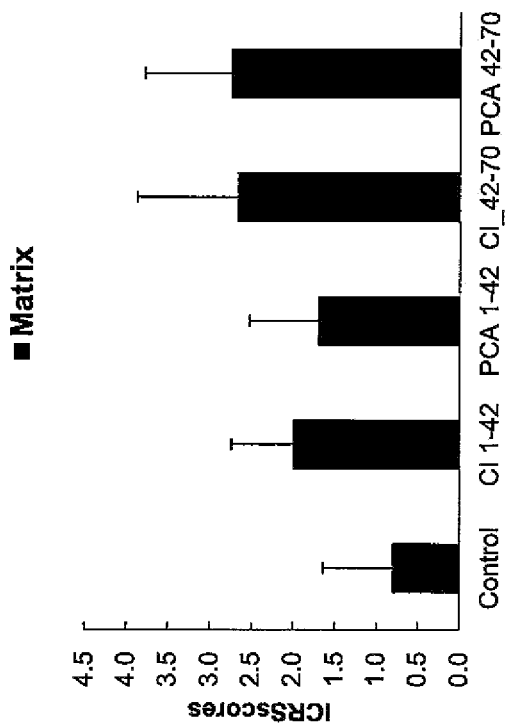
FIG. 22 provides a graph of ICRS histological visual scale scores for the cell matrix. Scores for all four groups improved.
Figure 23:
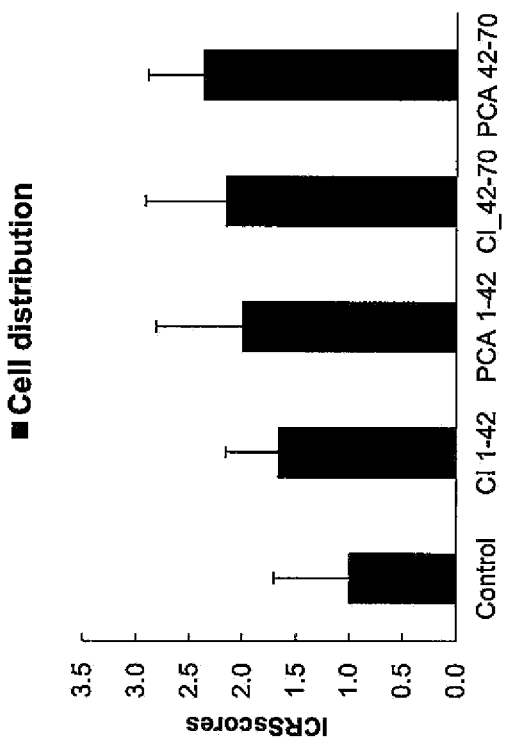
FIG. 23 provides a graph of ICRS histological visual scale scores for cell distribution. Cell distribution for all four groups improved.
Figure 24:
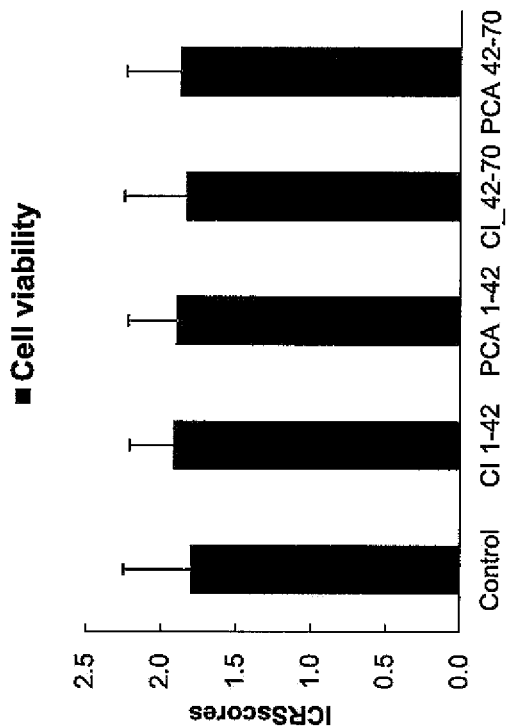
FIG. 24 provides a graph of ICRS histological visual scale scores for the cell viability. Cell viability remained the same for all four groups.
Figure 25:
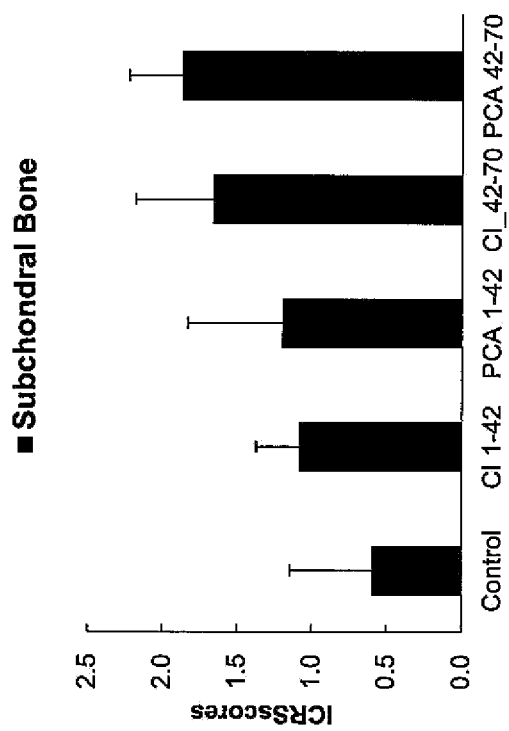
FIG. 25 provides a graph of ICRS histological visual scale scores for the subchondral bone. Scores for all four groups improved.
Figure 26:
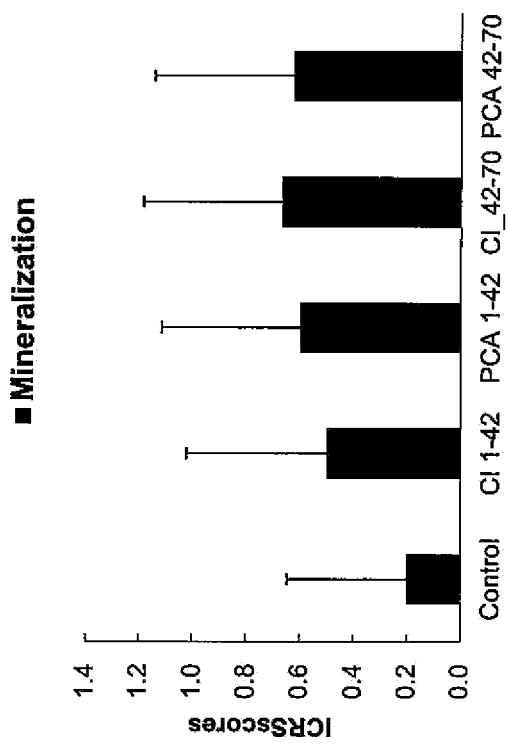
FIG. 26 provides a graph of ICRS histological visual scale scores for the Mineralization.

FIG. 20 shows increased expression of aggrecan in patellar cartilage of all four groups.

White Blood Cell Studies—Anti-Inflammatory Effects

In addition to testing for the increase or decrease of various factors and cytokines, tests were run to count the number of white blood cells, including polymorphonuclear leukocytes (PMN), macrophages (Mac) and lymphocytes (Lym). Lymphocyte and macrophage cell numbers increase when there is inflammation, and they are involved in the release of catabolic cytokines that are released into the joint.

FIG. 30 and FIG. 31D show that the total white blood cell count in the synovial fluid was decreased in all 4 study groups as well as the numbers of macrophages was also decreased (see FIG. 31B). FIG. 31C shows that the number of lymphocytes in the synovial fluid was also decreased in 3 of the groups (both the PCA groups and the C3G therapeutic group). FIG. 31A shows that the number of PMN s was also reduced in the synovial fluid of all four groups, although most noticeable in the C3G groups.

Discussion

The hypothesis was confirmed. There was significant reduction in the inflammation as measured by the white blood count and differential cell count. The synovium showed enhancement of the anabolic genes with a corresponding inhibition of the catabolic genes. The synovial fluid reflected the alteration with an increase in anabolic cytokines and a corresponding decrease in catabolic cytokines. The articular cartilage responded with histochemical and ICRS histological scoring evidence of enhanced nutrition and resultant protection of the patellar articular cartilage from the treatments. Medial or lateral compartment cartilage were not studied because they were directly affected by the surgical procedure and the patella was spared from the surgical intervention.

The dosage given was effective for both C3G and PCA. The regimen of five times per week proved practical and effective. There was an apparent benefit seen in the results of the 6-week duration of the prophylactic group versus the shorter 4 week duration in the therapeutic groups. This may indicate a longer duration has greater potential for intra-articular change.

The failure of healing of the partial thickness lateral femoral condylar laceration was not unexpected. The duration of the study was short. The space within a laceration is minimal so as not to house or hold blood or cells. In addition, there is constant shearing motion of the laceration as well as weight bearing forces. Such healing would likely require addition of cells in a blood clot with immobilization to reduce the shearing forces and a much longer period of time for restoration. It has been reported that fibrocartilage repair existed for as long as six years and conversion to hyaline cartilage was seen at 20 years. Johnson L L, Delano M C, Spector M, Jeng L, Pittsley A, Gottschalk A. The biological response following autogenous bone grafting for large volume defects of the Knee: index surgery through 12-21-year follow-up. Cartilage Volume 3 Issue 1. January 2012. Pp 85-98. First published on Aug. 16, 2011, as DOI: 10.1177119476035114113568.

Example 2: CRP Studies

C-reactive protein (CRP) is a protein found in the blood plasma, the levels of which rise in response to inflammation (i.e., C-reactive protein is an acute-phase protein). Its physiological role is to bind to phosphocholine expressed on the surface of dead or dying cells (and some types of bacteria) in order to activate the complement system via the C1Q complex. CRP rises within two hours of the onset of inflammation, up to a 50,000-fold, and peaks at 48 hours. Its half-life of 48 hours is constant, and therefore its level is determined by the rate of production and hence the severity of the precipitating cause. CRP is thus a screen for inflammation.

Knee surgery was performed to create a severe irreparable degenerative knee joint, which in turn elevated the CRP in the plasma to average of 8.8 mg/mL. A historical normal amount of CRP is 3.15 micrograms/mL. See Sun H, et al., Am J Pathol. October 2005; 167(4): 1139-1148. Rabbit CRP levels are close to the mean values of healthy middle-aged humans (2.82 mg/L) reported in the literature. See Ockene I S, et al., Clin Chem. 2001; 47:444-450.

The controls in the study were animals that had surgery and received no treatment. The prophylaxis test groups had the surgery and received 6 weeks of oral C-3-G or PCA 7 times per week as described in example 1. The therapeutic treatment group had surgery, received no treatment for 41 days and then at day 42 received oral C-3-G or PCA 7 times per week as described in example 1.

The CRP levels measured for the control group at 42 days (those receiving no treatment) showed an increase over normal levels: 8.8 mg/mL. The levels for the prophylaxis test group after treatment were reduced down to normal levels as follows:

Cyanidin-3-glucoside: CRP 3.1 micrograms/mL
Protocatechuic acid: CRP 3.6 micrograms/mL This shows that the initiation of the treatment at time zero did not allow the CRP to be elevated, in fact the levels decreased.

The therapeutic group had the surgery but received no treatment for 6 weeks and then received treatment for 4 weeks with same dosages of C3G or PCA that were used in the prophylaxis test groups. The plasma CRP levels the patients had very elevated levels. The plasma CRP was greatly elevated to 28.3 and 43 mg/mL (for the C3G and the PCA treatment groups, respectively). Thus, when the treatment was deferred for 6 weeks there was no effect on lowering the CRP, and in fact was elevated.

Thus, when C3G or PCA was given by oral route to a mammal immediately after injury, CRP, an indicator of inflammation was kept to normal levels (non-inflammatory levels).

While this disclosure includes specific examples, it will be apparent after an understanding of the disclosure of this application has been attained that various changes in form and details may be made in these examples without departing from the spirit and scope of the claims and their equivalents.

The invention claimed is:

1. A method for treating or reducing the severity of a joint injury or disease in a mammal comprising: orally administering a composition consisting of protocatechuic acid in a capsule to the mammal, wherein the composition is at least 0.035 mmol protocatechuic acid per kilogram bodyweight of the mammal.

2. The method of claim 1, wherein the administration of the composition increases insulin-like growth factor-1 (IGF-1) in the bloodstream of the mammal.

3. The method of claim 1, wherein the administration of the composition provides a chondronutritive effect in the synovial joint.

4. The method of claim 1, wherein the administration of the composition provides an improvement in a structure of an articular cartilage and a subchondral bone as assessed by International Cartilage Repair Society (ICRS) criteria.

5. The method of claim 1, wherein the administration of the composition increases articular cartilage anabolism in the synovial joint comprising producing increased amounts of lubricin on the cartilage surface.

6. The method of claim 1, wherein the administration of the composition increases cartilage anabolism in the synovial joint, comprising producing type II collagen in an articular cartilage matrix.

7. The method of claim 1, wherein the administration of the composition comprises producing aggrecan in the articular cartilage matrix.

8. The method of claim 1, wherein the administration of the composition comprises retention of normal subchondral bone without increased density and or osteophytes.

9. The method of claim 1, wherein the composition is between about 0.035 mmol and 0.200 mmol protocatechuic acid per kilogram bodyweight of the mammal.

10. The method of claim 1, wherein the composition is about 0.177 mmol protocatechuic acid per kilogram bodyweight of the mammal.

11. The method of claim 1, wherein the treating or reducing the severity of a joint injury includes an injury or disease of an articular cartilage.

12. The method of claim 9, wherein the oral administration comprises administering one or more of the capsules daily for at least 4 weeks.

13. The method of claim 9, wherein the oral administration comprises administering one or more of the capsules daily for at least 6 weeks.

14. The method of claim 9, wherein the oral administration comprises administering one or more of the capsules daily for at least 10 weeks.

15. The method of claim 9, wherein the oral administration comprises administering one or more of the capsules daily for at least one week before a surgery and continuing for at least 4 weeks after the surgery.

* * * * *